(12) United States Patent
Xu et al.

(10) Patent No.: US 10,294,479 B2
(45) Date of Patent: May 21, 2019

(54) *CANDIDA* CARBONYL REDUCTASE AND METHOD FOR PREPARING (R)-LIPOIC ACID PRECURSOR

(71) Applicant: East China University of Science and Technology, Shanghai (CN)

(72) Inventors: Jianhe Xu, Shanghai (CN); Yujun Zhang, Shanghai (CN); Gaowei Zheng, Shanghai (CN); Jiang Pan, Shanghai (CN)

(73) Assignee: East China University of Science and Technology, Shanghai (CN)

( * ) Notice: Subject to any disclaimer, the term of this patent is extended or adjusted under 35 U.S.C. 154(b) by 0 days.

(21) Appl. No.: 15/307,455

(22) PCT Filed: Mar. 4, 2015

(86) PCT No.: PCT/CN2015/073615
§ 371 (c)(1),
(2) Date: Oct. 28, 2016

(87) PCT Pub. No.: WO2016/138641
PCT Pub. Date: Sep. 9, 2016

(65) Prior Publication Data
US 2018/0265875 A1   Sep. 20, 2018

(51) Int. Cl.
| | |
|---|---|
| *C12N 9/04* | (2006.01) |
| *C12N 9/88* | (2006.01) |
| *C12N 9/10* | (2006.01) |
| *C12N 15/00* | (2006.01) |
| *C12P 7/62* | (2006.01) |
| *C12P 7/04* | (2006.01) |
| *C12N 15/52* | (2006.01) |
| *C12R 1/72* | (2006.01) |
| *C12N 1/16* | (2006.01) |
| *C12P 7/42* | (2006.01) |
| *C12N 9/02* | (2006.01) |
| *C12N 15/81* | (2006.01) |

(52) U.S. Cl.
CPC ............. *C12N 15/52* (2013.01); *C12N 1/16* (2013.01); *C12N 9/0036* (2013.01); *C12N 15/81* (2013.01); *C12P 7/42* (2013.01); *C12R 1/72* (2013.01); *C12Y 101/01184* (2013.01)

(58) Field of Classification Search
CPC .... C12N 9/04; C12N 9/10; C12N 9/88; C12P 7/62; C12P 7/04
See application file for complete search history.

(56) References Cited

U.S. PATENT DOCUMENTS

| | | |
|---|---|---|
| 7,135,328 B2 | 11/2006 | Olbrich et al. |
| 7,157,253 B2 | 1/2007 | Muller et al. |

FOREIGN PATENT DOCUMENTS

| | | |
|---|---|---|
| CN | 1884502 | 12/2006 |
| CN | 102618513 | 8/2012 |
| CN | 103451124 | 12/2013 |
| CN | 103849574 | 6/2014 |
| CN | 104099305 | 10/2014 |
| WO | 2005/049816 | 2/2005 |
| WO | 2007/028729 | 3/2007 |

OTHER PUBLICATIONS

Elliott, et al., "Asymmetric Synthesis Via Acetal Templates. 12. Highly Diastereoselective Coupling Reactions with a Ketene Acetal. An Efficient, Asymmetric Synthesis of R-(+)-α-lipoic acid," Tetrahedron Letters, vol. 26, issue 21, pp. 2535-2538, 1985.
Gopalan, et al., "Bakers' Yeast Reduction of Alkyl 6-Chloro-3-oxohexanoates: Synthesis of (R)—(+)-a-Lipoic Acid," J. Chem. Soc. Perkin Trans., pp. 1897-1990, Jan. 1990.
Zhang, et al., "Synthesis of optically pure S-sulfoxide by *Escherichia coli* transformant cells coexpressing the P450 monooxygenase and glucose dehydrogenase genes," J. Ind. Microbiol Biotechnol., vol. 38, pp. 633-641, 2011.
Ma, et al. "Stereospecific Reduction of Methyl o-Chlorobenzoylformate at 300 g•L1 without Additional Cofactor using a carbonyl Reductase Mined from Candida glabrata," Adv. Synth. Catal., vol. 354, pp. 1765-1772, 2012.
Goldberg, et al., "Biocatalytic ketone reduction—a powerful tool for the production of chiral alcohols—part I: Processes with isolated enzymes," Appl. Microbiol. Biotechnol., vol. 76, pp. 237-248, 2007.
Guida, et al., "Hypothetical protein CPAR2_104460 [Candida parapsilosis]," NCBI Genbank, Oct. 26, 2011, abstract.
Guida, et al., "Candida parapsilosis strain CDC317 annotated contig 005569," NCBI Genbank, Oct. 26, 2011, abstract.
International Search Report in related application PCT/CN2015/073615, dated Nov. 30, 2015, 4 pages.
Search Report in corresponding CN 201580000265.X, dated Nov. 19, 2018.
Huang, "Molecular engineering and application of Candida glabrata keto ester reductase for bioreduction of aromatic a-keto esters", Sep. 15, 2014, English abstract attached.

*Primary Examiner* — Maryam Monshipouri
(74) *Attorney, Agent, or Firm* — Hovey Williams LLP

(57) ABSTRACT

Disclosed herein is *Candida parapsilosis* CGMCC 9630, the carbonyl reductase expressed by said strain and the encoding gene and amino acid sequence thereof, the recombinant expression vector and recombinant expression transformant containing said gene sequence, and use of whole cells of *Candida parapsilosis*, carbonyl reductase or corresponding recombinant transformant thereof as catalyst in catalyzing asymmetric reduction of prochiral carbonyl compounds, particularly reduction of 6-carbonyl-8-halogenocaprylate to prepare the synthetic precursor of (R)-α-lipoic acid, (R)-6-hydroxy-8-halogenocaprylate. In comparison to other methods of asymmetric reduction for preparing (R)-6-hydroxy-8-halogenocaprylate, the disclosure has advantages of high substrate concentration, mild reaction conditions, environmental friendship, high yield, and high optical purity of the product, and thus has good prospect in industrial production of (R)-α-α-lipoic acid.

10 Claims, 1 Drawing Sheet
Specification includes a Sequence Listing.

SEQUENCE LISTING

<160> NUMBER OF SEQ ID NOS: 14

<210> SEQ ID NO 1
<211> LENGTH: 1002
<212> TYPE: DNA
<213> ORGANISM: Candida parapsilosis
<220> FEATURE:
<221> NAME/KEY: CDS
<222> LOCATION: (1)..(1002)

<400> SEQUENCE: 1

```
atg aca gta ttt gtc tca ggt gca aca ggc ttc att gct cag cac gta      48
Met Thr Val Phe Val Ser Gly Ala Thr Gly Phe Ile Ala Gln His Val
1               5                   10                  15 gtt aag gaa ctc ttg aga cag ggt ttc caa gtg att ggt tca gtt aga      96
Val Lys Glu Leu Leu Arg Gln Gly Phe Gln Val Ile Gly Ser Val Arg
            20                  25                  30
```

| | | |
|---|---|---|
| aca aaa aca aag ggt gac tat ttg tcg aag tta atc agt tca aag agt<br>Thr Lys Thr Lys Gly Asp Tyr Leu Ser Lys Leu Ile Ser Ser Lys Ser<br>35                      40                        45 | | 144 |
| ttt tct tac gtg gtg gta cct gat atc gcg tca aaa ggt gcc ttt gat<br>Phe Ser Tyr Val Val Val Pro Asp Ile Ala Ser Lys Gly Ala Phe Asp<br>50                      55                        60 | | 192 |
| cag gtt tta caa gac aac gaa aat att gag agt ttt att cac aca gca<br>Gln Val Leu Gln Asp Asn Glu Asn Ile Glu Ser Phe Ile His Thr Ala<br>65                      70                      75                      80 | | 240 |
| agt cca gtt gat ttc ggg gtt agt gat ata caa act ggt ctt ttg gat<br>Ser Pro Val Asp Phe Gly Val Ser Asp Ile Gln Thr Gly Leu Leu Asp<br>                      85                      90                      95 | | 288 |
| cca gca ata gag gga acc aaa aac gtg ttg gaa gca att gac aag ttt<br>Pro Ala Ile Glu Gly Thr Lys Asn Val Leu Glu Ala Ile Asp Lys Phe<br>                100                    105                    110 | | 336 |
| ggc agc aat gta aag agc atc gtt gtt acg tcg tca aca tcg gct gtt<br>Gly Ser Asn Val Lys Ser Ile Val Val Thr Ser Ser Thr Ser Ala Val<br>            115                    120                    125 | | 384 |
| cgt gat tca agc ggc aac aga cct tcg aat agt aca tta gaa gaa tcc<br>Arg Asp Ser Ser Gly Asn Arg Pro Ser Asn Ser Thr Leu Glu Glu Ser<br>130                     135                    140 | | 432 |
| gct tgg aac gaa atc acc att gag caa ggc ttg aaa agc acg agg ttg<br>Ala Trp Asn Glu Ile Thr Ile Glu Gln Gly Leu Lys Ser Thr Arg Leu<br>145                     150                    155                    160 | | 480 |
| ggt tat gct gca gcc aaa act ttt gct gag aag gaa gtt tgg aag ttt<br>Gly Tyr Ala Ala Ala Lys Thr Phe Ala Glu Lys Glu Val Trp Lys Phe<br>                165                    170                    175 | | 528 |
| gct aat gca cac acg ggt ttc aat gtg aca acc gtc aat cca act ttt<br>Ala Asn Ala His Thr Gly Phe Asn Val Thr Thr Val Asn Pro Thr Phe<br>            180                    185                    190 | | 576 |
| gta ttt ggc cct caa gcg tac gag gta aaa cat aaa gag aag cta aat<br>Val Phe Gly Pro Gln Ala Tyr Glu Val Lys His Lys Glu Lys Leu Asn<br>195                     200                    205 | | 624 |
| gag tca gca gag atc atc aac aaa gtt ttg aac ttg agt cca gat gac<br>Glu Ser Ala Glu Ile Ile Asn Lys Val Leu Asn Leu Ser Pro Asp Asp<br>210                     215                    220 | | 672 |
| gct atc cct aga ctt acc gga tta tac att gat gtc aga gat gtg gca<br>Ala Ile Pro Arg Leu Thr Gly Leu Tyr Ile Asp Val Arg Asp Val Ala<br>225                     230                    235                    240 | | 720 |
| aaa gct cat gtt gct gct gtt aac cac cca aat cag ttc aat ggg caa<br>Lys Ala His Val Ala Ala Val Asn His Pro Asn Gln Phe Asn Gly Gln<br>                245                    250                    255 | | 768 |
| agg ttg tta ctc att gac tcg gca tgg acc aat gaa ctt ctt gct gtt<br>Arg Leu Leu Leu Ile Asp Ser Ala Trp Thr Asn Glu Leu Leu Ala Val<br>            260                    265                    270 | | 816 |
| att att aac aaa cat ttt cca aat gct gac att cca aaa gga agt att<br>Ile Ile Asn Lys His Phe Pro Asn Ala Asp Ile Pro Lys Gly Ser Ile<br>275                     280                    285 | | 864 |
| gag aaa agt gat gaa gaa ttg aag aaa gca aat ctg aaa tgg gac aat<br>Glu Lys Ser Asp Glu Glu Leu Lys Lys Ala Asn Leu Lys Trp Asp Asn<br>290                     295                    300 | | 912 |
| gcc aaa act aaa aag ctt ttg ggt ttt gag ttt att cca ctt gaa aaa<br>Ala Lys Thr Lys Lys Leu Leu Gly Phe Glu Phe Ile Pro Leu Glu Lys<br>305                     310                    315                    320 | | 960 |
| tcg gta gtt gac gca gtt aaa caa ctt ctc gat gcc aag taa<br>Ser Val Val Asp Ala Val Lys Gln Leu Leu Asp Ala Lys<br>                325                    330 | | 1002 |

<210> SEQ ID NO 2
<211> LENGTH: 333

<212> TYPE: PRT
<213> ORGANISM: Candida parapsilosis

<400> SEQUENCE: 2

```
Met Thr Val Phe Val Ser Gly Ala Thr Gly Phe Ile Ala Gln His Val
1               5                   10                  15

Val Lys Glu Leu Leu Arg Gln Gly Phe Gln Val Ile Gly Ser Val Arg
            20                  25                  30

Thr Lys Thr Lys Gly Asp Tyr Leu Ser Lys Leu Ile Ser Ser Lys Ser
        35                  40                  45

Phe Ser Tyr Val Val Pro Asp Ile Ala Ser Lys Gly Ala Phe Asp
    50                  55                  60

Gln Val Leu Gln Asp Asn Glu Asn Ile Glu Ser Phe Ile His Thr Ala
65                  70                  75                  80

Ser Pro Val Asp Phe Gly Val Ser Asp Ile Gln Thr Gly Leu Leu Asp
                85                  90                  95

Pro Ala Ile Glu Gly Thr Lys Asn Val Leu Glu Ala Ile Asp Lys Phe
            100                 105                 110

Gly Ser Asn Val Lys Ser Ile Val Val Thr Ser Ser Thr Ser Ala Val
        115                 120                 125

Arg Asp Ser Ser Gly Asn Arg Pro Ser Asn Ser Thr Leu Glu Glu Ser
130                 135                 140

Ala Trp Asn Glu Ile Thr Ile Glu Gln Gly Leu Lys Ser Thr Arg Leu
145                 150                 155                 160

Gly Tyr Ala Ala Ala Lys Thr Phe Ala Glu Lys Glu Val Trp Lys Phe
                165                 170                 175

Ala Asn Ala His Thr Gly Phe Asn Val Thr Thr Val Asn Pro Thr Phe
            180                 185                 190

Val Phe Gly Pro Gln Ala Tyr Glu Val Lys His Lys Glu Lys Leu Asn
        195                 200                 205

Glu Ser Ala Glu Ile Ile Asn Lys Val Leu Asn Leu Ser Pro Asp Asp
210                 215                 220

Ala Ile Pro Arg Leu Thr Gly Leu Tyr Ile Asp Val Arg Asp Val Ala
225                 230                 235                 240

Lys Ala His Val Ala Ala Val Asn His Pro Asn Gln Phe Asn Gly Gln
                245                 250                 255

Arg Leu Leu Leu Ile Asp Ser Ala Trp Thr Asn Glu Leu Leu Ala Val
            260                 265                 270

Ile Ile Asn Lys His Phe Pro Asn Ala Asp Ile Pro Lys Gly Ser Ile
        275                 280                 285

Glu Lys Ser Asp Glu Glu Leu Lys Lys Ala Asn Leu Lys Trp Asp Asn
290                 295                 300

Ala Lys Thr Lys Lys Leu Leu Gly Phe Glu Phe Ile Pro Leu Glu Lys
305                 310                 315                 320

Ser Val Val Asp Ala Val Lys Gln Leu Leu Asp Ala Lys
                325                 330
```

<210> SEQ ID NO 3
<211> LENGTH: 1002
<212> TYPE: DNA
<213> ORGANISM: Artificial Sequence
<220> FEATURE:
<223> OTHER INFORMATION: Carbonyl reductase mutant gene
<220> FEATURE:
<221> NAME/KEY: CDS
<222> LOCATION: (1)..(1002)

<400> SEQUENCE: 3

| | | | | | | | | | | | | | | | | |
|---|---|---|---|---|---|---|---|---|---|---|---|---|---|---|---|---|
| atg | aca | gta | ttt | gtc | tca | ggt | gca | aca | ggc | ttc | att | gct | cag | cac | gta | 48 |
| Met | Thr | Val | Phe | Val | Ser | Gly | Ala | Thr | Gly | Phe | Ile | Ala | Gln | His | Val | |
| 1 | | | | 5 | | | | | 10 | | | | | 15 | | |
| gtt | aag | gaa | ctc | ttg | aga | cag | ggt | ttt | caa | gtg | att | ggt | tca | gtt | aga | 96 |
| Val | Lys | Glu | Leu | Leu | Arg | Gln | Gly | Phe | Gln | Val | Ile | Gly | Ser | Val | Arg | |
| | | | | 20 | | | | | 25 | | | | | 30 | | |
| aca | aaa | aca | aag | ggt | gac | tat | ttg | tcg | aag | tta | atc | agt | tca | aag | agt | 144 |
| Thr | Lys | Thr | Lys | Gly | Asp | Tyr | Leu | Ser | Lys | Leu | Ile | Ser | Ser | Lys | Ser | |
| | | 35 | | | | | 40 | | | | | 45 | | | | |
| ttt | tct | tac | gtg | gtg | gta | cct | gat | atc | gcg | tca | aaa | ggt | gcc | ttt | gat | 192 |
| Phe | Ser | Tyr | Val | Val | Val | Pro | Asp | Ile | Ala | Ser | Lys | Gly | Ala | Phe | Asp | |
| | 50 | | | | | 55 | | | | | 60 | | | | | |
| cag | gtt | tta | caa | gac | aac | gaa | aat | att | gag | agt | ttt | att | cac | aca | gca | 240 |
| Gln | Val | Leu | Gln | Asp | Asn | Glu | Asn | Ile | Glu | Ser | Phe | Ile | His | Thr | Ala | |
| 65 | | | | | 70 | | | | | 75 | | | | | 80 | |
| agt | cca | gtt | gat | ttc | gaa | gtt | agt | gat | ata | caa | act | ggt | ctt | ttg | gat | 288 |
| Ser | Pro | Val | Asp | Phe | Glu | Val | Ser | Asp | Ile | Gln | Thr | Gly | Leu | Leu | Asp | |
| | | | | 85 | | | | | 90 | | | | | 95 | | |
| cca | gca | ata | gag | gga | acc | aaa | aac | gtg | ttg | gaa | gca | att | gac | aag | ttt | 336 |
| Pro | Ala | Ile | Glu | Gly | Thr | Lys | Asn | Val | Leu | Glu | Ala | Ile | Asp | Lys | Phe | |
| | | | 100 | | | | | 105 | | | | | 110 | | | |
| ggc | agc | aat | gta | aag | agc | atc | gtt | gtt | acg | tcg | tca | aca | tcg | gct | gtt | 384 |
| Gly | Ser | Asn | Val | Lys | Ser | Ile | Val | Val | Thr | Ser | Ser | Thr | Ser | Ala | Val | |
| | | | | 115 | | | | | 120 | | | | | 125 | | |
| cgt | gat | tca | agc | ggc | aac | aga | cct | tcg | aat | agt | aca | tta | gaa | gaa | tcc | 432 |
| Arg | Asp | Ser | Ser | Gly | Asn | Arg | Pro | Ser | Asn | Ser | Thr | Leu | Glu | Glu | Ser | |
| | 130 | | | | | 135 | | | | | 140 | | | | | |
| gct | tgg | aac | gaa | atc | acc | att | gag | caa | ggc | ttg | aaa | agc | acg | agg | ttg | 480 |
| Ala | Trp | Asn | Glu | Ile | Thr | Ile | Glu | Gln | Gly | Leu | Lys | Ser | Thr | Arg | Leu | |
| 145 | | | | | 150 | | | | | 155 | | | | | 160 | |
| ggt | tat | gct | gca | gcc | aaa | act | ttt | gct | gag | aag | gaa | gtt | tgg | aag | ttt | 528 |
| Gly | Tyr | Ala | Ala | Ala | Lys | Thr | Phe | Ala | Glu | Lys | Glu | Val | Trp | Lys | Phe | |
| | | | | 165 | | | | | 170 | | | | | 175 | | |
| gct | aat | gca | cac | acg | ggt | ttc | aat | gtg | aca | acc | gtc | aat | cca | act | ttt | 576 |
| Ala | Asn | Ala | His | Thr | Gly | Phe | Asn | Val | Thr | Thr | Val | Asn | Pro | Thr | Phe | |
| | | | 180 | | | | | 185 | | | | | 190 | | | |
| gta | ttt | ggc | cct | caa | gcg | tac | gag | gta | aaa | cat | aaa | gag | aag | cta | aat | 624 |
| Val | Phe | Gly | Pro | Gln | Ala | Tyr | Glu | Val | Lys | His | Lys | Glu | Lys | Leu | Asn | |
| | | | | 195 | | | | | 200 | | | | | 205 | | |
| gag | tca | gca | gag | atc | atc | aac | aaa | gtt | ttg | aac | ttg | agt | cca | gat | gac | 672 |
| Glu | Ser | Ala | Glu | Ile | Ile | Asn | Lys | Val | Leu | Asn | Leu | Ser | Pro | Asp | Asp | |
| | 210 | | | | | 215 | | | | | 220 | | | | | |
| gct | atc | cct | aga | ctt | acc | gga | tta | tac | att | gat | gtc | aga | gat | gtg | gca | 720 |
| Ala | Ile | Pro | Arg | Leu | Thr | Gly | Leu | Tyr | Ile | Asp | Val | Arg | Asp | Val | Ala | |
| 225 | | | | | 230 | | | | | 235 | | | | | 240 | |
| aaa | gct | cat | gtt | gct | gct | gtt | aac | cac | cca | aat | cag | ttc | aat | ggg | caa | 768 |
| Lys | Ala | His | Val | Ala | Ala | Val | Asn | His | Pro | Asn | Gln | Phe | Asn | Gly | Gln | |
| | | | | 245 | | | | | 250 | | | | | 255 | | |
| agg | ttg | tta | ctc | att | gac | tcg | gca | tgg | acc | aat | gaa | ctt | ctt | gct | gtt | 816 |
| Arg | Leu | Leu | Leu | Ile | Asp | Ser | Ala | Trp | Thr | Asn | Glu | Leu | Leu | Ala | Val | |
| | | | 260 | | | | | 265 | | | | | 270 | | | |
| att | att | aac | aaa | cat | ttt | cca | aat | gct | gac | att | cca | aaa | gga | agt | att | 864 |
| Ile | Ile | Asn | Lys | His | Phe | Pro | Asn | Ala | Asp | Ile | Pro | Lys | Gly | Ser | Ile | |
| | | | | 275 | | | | | 280 | | | | | 285 | | |
| gag | aaa | agt | gat | gaa | gaa | ttg | aag | aaa | gca | aat | ctg | aaa | tgg | gac | aat | 912 |
| Glu | Lys | Ser | Asp | Glu | Glu | Leu | Lys | Lys | Ala | Asn | Leu | Lys | Trp | Asp | Asn | |
| | 290 | | | | | 295 | | | | | 300 | | | | | |
| gcc | aaa | act | aaa | aag | ctt | ttg | ggt | ttt | gag | ttt | att | cca | ctt | gaa | aaa | 960 |

```
Ala Lys Thr Lys Lys Leu Leu Gly Phe Glu Phe Ile Pro Leu Glu Lys
305                 310                 315                 320 tcg gta gtt gac gca gtt aaa caa ctt ctc gat gcc aag taa          1002
Ser Val Val Asp Ala Val Lys Gln Leu Leu Asp Ala Lys
                325                 330
```

<210> SEQ ID NO 4
<211> LENGTH: 333
<212> TYPE: PRT
<213> ORGANISM: Artificial Sequence
<220> FEATURE:
<223> OTHER INFORMATION: Synthetic construct

<400> SEQUENCE: 4

```
Met Thr Val Phe Val Ser Gly Ala Thr Gly Phe Ile Ala Gln His Val
1               5                   10                  15

Val Lys Glu Leu Leu Arg Gln Gly Phe Gln Val Ile Gly Ser Val Arg
            20                  25                  30

Thr Lys Thr Lys Gly Asp Tyr Leu Ser Lys Leu Ile Ser Ser Lys Ser
        35                  40                  45

Phe Ser Tyr Val Val Pro Asp Ile Ala Ser Lys Gly Ala Phe Asp
50                  55                  60

Gln Val Leu Gln Asp Asn Glu Asn Ile Glu Ser Phe Ile His Thr Ala
65                  70                  75                  80

Ser Pro Val Asp Phe Glu Val Ser Asp Ile Gln Thr Gly Leu Leu Asp
                85                  90                  95

Pro Ala Ile Glu Gly Thr Lys Asn Val Leu Glu Ala Ile Asp Lys Phe
            100                 105                 110

Gly Ser Asn Val Lys Ser Ile Val Val Thr Ser Ser Thr Ser Ala Val
        115                 120                 125

Arg Asp Ser Ser Gly Asn Arg Pro Ser Asn Ser Thr Leu Glu Glu Ser
130                 135                 140

Ala Trp Asn Glu Ile Thr Ile Glu Gln Gly Leu Lys Ser Thr Arg Leu
145                 150                 155                 160

Gly Tyr Ala Ala Ala Lys Thr Phe Ala Glu Lys Glu Val Trp Lys Phe
                165                 170                 175

Ala Asn Ala His Thr Gly Phe Asn Val Thr Thr Val Asn Pro Thr Phe
            180                 185                 190

Val Phe Gly Pro Gln Ala Tyr Glu Val Lys His Lys Glu Lys Leu Asn
        195                 200                 205

Glu Ser Ala Glu Ile Ile Asn Lys Val Leu Asn Leu Ser Pro Asp Asp
210                 215                 220

Ala Ile Pro Arg Leu Thr Gly Leu Tyr Ile Asp Val Arg Asp Val Ala
225                 230                 235                 240

Lys Ala His Val Ala Ala Val Asn His Pro Asn Gln Phe Asn Gly Gln
                245                 250                 255

Arg Leu Leu Leu Ile Asp Ser Ala Trp Thr Asn Glu Leu Leu Ala Val
            260                 265                 270

Ile Ile Asn Lys His Phe Pro Asn Ala Asp Ile Pro Lys Gly Ser Ile
        275                 280                 285

Glu Lys Ser Asp Glu Glu Leu Lys Lys Ala Asn Leu Trp Asp Asn
290                 295                 300

Ala Lys Thr Lys Lys Leu Leu Gly Phe Glu Phe Ile Pro Leu Glu Lys
305                 310                 315                 320

Ser Val Val Asp Ala Val Lys Gln Leu Leu Asp Ala Lys
                325                 330
```

```
<210> SEQ ID NO 5
<211> LENGTH: 1002
<212> TYPE: DNA
<213> ORGANISM: Artificial Sequence
<220> FEATURE:
<223> OTHER INFORMATION: Carbonyl reductase mutant gene
<220> FEATURE:
<221> NAME/KEY: CDS
<222> LOCATION: (1)..(1002)

<400> SEQUENCE: 5
```

| | | | | | | | | | | | | | | | | |
|---|---|---|---|---|---|---|---|---|---|---|---|---|---|---|---|---|
| atg | aca | gta | ttt | gtc | tca | ggt | gca | aca | ggc | ttc | att | gct | cag | cac | gta | 48 |
| Met | Thr | Val | Phe | Val | Ser | Gly | Ala | Thr | Gly | Phe | Ile | Ala | Gln | His | Val | |
| 1 | | | | 5 | | | | | 10 | | | | | 15 | | |
| gtt | aag | gaa | ctc | ttg | aga | cag | ggt | ttt | caa | gtg | att | ggt | tca | gtt | aga | 96 |
| Val | Lys | Glu | Leu | Leu | Arg | Gln | Gly | Phe | Gln | Val | Ile | Gly | Ser | Val | Arg | |
| | | | 20 | | | | | 25 | | | | | 30 | | | |
| aca | aaa | aca | aag | ggt | gac | tat | ttg | tcg | aag | tta | atc | agt | tca | aag | agt | 144 |
| Thr | Lys | Thr | Lys | Gly | Asp | Tyr | Leu | Ser | Lys | Leu | Ile | Ser | Ser | Lys | Ser | |
| | | 35 | | | | | 40 | | | | | 45 | | | | |
| ttt | tct | tac | gtg | gtg | gta | cct | gat | atc | gcg | tca | aaa | ggt | gcc | ttt | gat | 192 |
| Phe | Ser | Tyr | Val | Val | Val | Pro | Asp | Ile | Ala | Ser | Lys | Gly | Ala | Phe | Asp | |
| 50 | | | | | 55 | | | | | 60 | | | | | | |
| cag | gtt | tta | caa | gac | aac | gaa | aat | att | gag | agt | ttt | att | cac | aca | gca | 240 |
| Gln | Val | Leu | Gln | Asp | Asn | Glu | Asn | Ile | Glu | Ser | Phe | Ile | His | Thr | Ala | |
| 65 | | | | | 70 | | | | | 75 | | | | | 80 | |
| agt | cca | gtt | gat | ttc | gaa | gtt | agt | gat | ata | caa | act | ggt | ctt | ttg | gat | 288 |
| Ser | Pro | Val | Asp | Phe | Glu | Val | Ser | Asp | Ile | Gln | Thr | Gly | Leu | Leu | Asp | |
| | | | | 85 | | | | | 90 | | | | | 95 | | |
| cca | gca | ata | gag | gga | acc | aaa | aac | gtg | ttg | gaa | gca | att | gac | aag | ttt | 336 |
| Pro | Ala | Ile | Glu | Gly | Thr | Lys | Asn | Val | Leu | Glu | Ala | Ile | Asp | Lys | Phe | |
| | | | 100 | | | | | 105 | | | | | 110 | | | |
| ggc | agc | aat | gta | aag | agc | atc | gtt | gtt | acg | tcg | tca | aca | tcg | gct | gtt | 384 |
| Gly | Ser | Asn | Val | Lys | Ser | Ile | Val | Val | Thr | Ser | Ser | Thr | Ser | Ala | Val | |
| | | 115 | | | | | 120 | | | | | 125 | | | | |
| cgt | gat | tca | agc | ggc | aac | aga | cct | tcg | aat | agt | aca | tta | gaa | gaa | tcc | 432 |
| Arg | Asp | Ser | Ser | Gly | Asn | Arg | Pro | Ser | Asn | Ser | Thr | Leu | Glu | Glu | Ser | |
| | 130 | | | | | 135 | | | | | 140 | | | | | |
| gct | tgg | aac | gaa | atc | acc | att | gag | caa | ggc | ttg | aaa | agc | acg | agg | ttg | 480 |
| Ala | Trp | Asn | Glu | Ile | Thr | Ile | Glu | Gln | Gly | Leu | Lys | Ser | Thr | Arg | Leu | |
| 145 | | | | | 150 | | | | | 155 | | | | | 160 | |
| ggt | tat | tcg | gca | gcc | aaa | act | ttt | gct | gag | aag | gaa | gtt | tgg | aag | ttt | 528 |
| Gly | Tyr | Ser | Ala | Ala | Lys | Thr | Phe | Ala | Glu | Lys | Glu | Val | Trp | Lys | Phe | |
| | | | | 165 | | | | | 170 | | | | | 175 | | |
| gct | aat | gca | cac | acg | ggt | ttc | aat | gtg | aca | acc | gtc | aat | cca | act | ttt | 576 |
| Ala | Asn | Ala | His | Thr | Gly | Phe | Asn | Val | Thr | Thr | Val | Asn | Pro | Thr | Phe | |
| | | | 180 | | | | | 185 | | | | | 190 | | | |
| gta | ttt | ggc | cct | caa | gcg | tac | gag | gta | aaa | cat | aaa | gag | aag | cta | aat | 624 |
| Val | Phe | Gly | Pro | Gln | Ala | Tyr | Glu | Val | Lys | His | Lys | Glu | Lys | Leu | Asn | |
| | | 195 | | | | | 200 | | | | | 205 | | | | |
| gag | tca | gca | gag | atc | atc | aac | aaa | gtt | ttg | aac | ttg | agt | cca | gat | gac | 672 |
| Glu | Ser | Ala | Glu | Ile | Ile | Asn | Lys | Val | Leu | Asn | Leu | Ser | Pro | Asp | Asp | |
| | 210 | | | | | 215 | | | | | 220 | | | | | |
| gct | atc | cct | aga | ctt | acc | gga | tta | tac | att | gat | gtc | aga | gat | gtg | gca | 720 |
| Ala | Ile | Pro | Arg | Leu | Thr | Gly | Leu | Tyr | Ile | Asp | Val | Arg | Asp | Val | Ala | |
| 225 | | | | | 230 | | | | | 235 | | | | | 240 | |
| aaa | gct | cat | gtt | gct | gct | gtt | aac | cac | cca | aat | cag | ttc | aat | ggg | caa | 768 |
| Lys | Ala | His | Val | Ala | Ala | Val | Asn | His | Pro | Asn | Gln | Phe | Asn | Gly | Gln | |
| | | | | 245 | | | | | 250 | | | | | 255 | | |
| agg | ttg | tta | ctc | att | gac | tcg | gca | tgg | acc | aat | gaa | ctt | ctt | gct | gtt | 816 |

```
Arg Leu Leu Leu Ile Asp Ser Ala Trp Thr Asn Glu Leu Leu Ala Val
            260                 265                 270 att att aac aaa cat ttt cca aat gct gac att cca aaa gga agt att      864
Ile Ile Asn Lys His Phe Pro Asn Ala Asp Ile Pro Lys Gly Ser Ile
            275                 280                 285 gag aaa agt gat gaa gaa ttg aag aaa gca aat ctg aaa tgg gac aat      912
Glu Lys Ser Asp Glu Glu Leu Lys Lys Ala Asn Leu Lys Trp Asp Asn
        290                 295                 300 gcc aaa act aaa aag ctt ttg ggt ttt gag ttt att cca ctt gaa aaa      960
Ala Lys Thr Lys Lys Leu Leu Gly Phe Glu Phe Ile Pro Leu Glu Lys
305                 310                 315                 320 tcg gta gtt gac gca gtt aaa caa ctt ctc gat gcc aag taa             1002
Ser Val Val Asp Ala Val Lys Gln Leu Leu Asp Ala Lys
                    325                 330
```

<210> SEQ ID NO 6
<211> LENGTH: 333
<212> TYPE: PRT
<213> ORGANISM: Artificial Sequence
<220> FEATURE:
<223> OTHER INFORMATION: Synthetic construct

<400> SEQUENCE: 6

```
Met Thr Val Phe Val Ser Gly Ala Thr Gly Phe Ile Ala Gln His Val
1               5                   10                  15

Val Lys Glu Leu Leu Arg Gln Gly Phe Gln Val Ile Gly Ser Val Arg
            20                  25                  30

Thr Lys Thr Lys Gly Asp Tyr Leu Ser Lys Leu Ile Ser Ser Lys Ser
        35                  40                  45

Phe Ser Tyr Val Val Val Pro Asp Ile Ala Ser Lys Gly Ala Phe Asp
    50                  55                  60

Gln Val Leu Gln Asp Asn Glu Asn Ile Glu Phe Ile His Thr Ala
65                  70                  75                  80

Ser Pro Val Asp Phe Glu Val Ser Asp Ile Gln Thr Gly Leu Leu Asp
                85                  90                  95

Pro Ala Ile Glu Gly Thr Lys Asn Val Leu Glu Ala Ile Asp Lys Phe
            100                 105                 110

Gly Ser Asn Val Lys Ser Ile Val Val Thr Ser Ser Thr Ser Ala Val
        115                 120                 125

Arg Asp Ser Ser Gly Asn Arg Pro Ser Asn Ser Thr Leu Glu Glu Ser
    130                 135                 140

Ala Trp Asn Glu Ile Thr Ile Glu Gln Gly Leu Lys Ser Thr Arg Leu
145                 150                 155                 160

Gly Tyr Ser Ala Ala Lys Thr Phe Ala Glu Lys Val Trp Lys Phe
                165                 170                 175

Ala Asn Ala His Thr Gly Phe Asn Val Thr Thr Val Asn Pro Thr Phe
            180                 185                 190

Val Phe Gly Pro Gln Ala Tyr Glu Val Lys His Lys Glu Lys Leu Asn
        195                 200                 205

Glu Ser Ala Glu Ile Ile Asn Lys Val Leu Asn Leu Ser Pro Asp Asp
    210                 215                 220

Ala Ile Pro Arg Leu Thr Gly Leu Tyr Ile Asp Val Arg Asp Val Ala
225                 230                 235                 240

Lys Ala His Val Ala Ala Val Asn His Pro Asn Gln Phe Asn Gly Gln
                245                 250                 255

Arg Leu Leu Leu Ile Asp Ser Ala Trp Thr Asn Glu Leu Leu Ala Val
            260                 265                 270
```

```
Ile Ile Asn Lys His Phe Pro Asn Ala Asp Ile Pro Lys Gly Ser Ile
        275                 280                 285

Glu Lys Ser Asp Glu Glu Leu Lys Lys Ala Asn Leu Lys Trp Asp Asn
290                 295                 300

Ala Lys Thr Lys Lys Leu Leu Gly Phe Glu Phe Ile Pro Leu Glu Lys
305                 310                 315                 320

Ser Val Val Asp Ala Val Lys Gln Leu Leu Asp Ala Lys
                325                 330
```

<210> SEQ ID NO 7
<211> LENGTH: 33
<212> TYPE: DNA
<213> ORGANISM: Artificial Sequence
<220> FEATURE:
<223> OTHER INFORMATION: Primer
<400> SEQUENCE: 7
ccggaattca tgacagtatt tgtctcaggt gca                                33

<210> SEQ ID NO 8
<211> LENGTH: 33
<212> TYPE: DNA
<213> ORGANISM: Artificial Sequence
<220> FEATURE:
<223> OTHER INFORMATION: Primer
<400> SEQUENCE: 8
ccgctcgagt tacttggcat cgagaagttg ttt                                33

<210> SEQ ID NO 9
<211> LENGTH: 33
<212> TYPE: DNA
<213> ORGANISM: Artificial Sequence
<220> FEATURE:
<223> OTHER INFORMATION: Primer
<400> SEQUENCE: 9
ggaattccat atgacagtat ttgtctcagg tgc                                33

<210> SEQ ID NO 10
<211> LENGTH: 33
<212> TYPE: DNA
<213> ORGANISM: Artificial Sequence
<220> FEATURE:
<223> OTHER INFORMATION: Primer
<400> SEQUENCE: 10
ccggaattct tacttggcat cgagaagttg ttt                                33

<210> SEQ ID NO 11
<211> LENGTH: 41
<212> TYPE: DNA
<213> ORGANISM: Artificial Sequence
<220> FEATURE:
<223> OTHER INFORMATION: Primer
<400> SEQUENCE: 11
acgcgtcgac aaggagatat aatgtataaa gatttagaag g                       41

<210> SEQ ID NO 12
<211> LENGTH: 31
<212> TYPE: DNA
<213> ORGANISM: Artificial Sequence
<220> FEATURE:

-continued

<223> OTHER INFORMATION: Primer

<400> SEQUENCE: 12
ccgctcgagt tatccgcgtc ctgcttggaa t　　　　　　　　　　　　　　　31

<210> SEQ ID NO 13
<211> LENGTH: 786
<212> TYPE: DNA
<213> ORGANISM: Bacillus megaterium
<220> FEATURE:
<221> NAME/KEY: CDS
<222> LOCATION: (1)..(786)

<400> SEQUENCE: 13

| atg | tat | aaa | gat | tta | gaa | gga | aaa | gta | gtg | gtc | ata | aca | ggt | tca | tct | 48 |
|---|---|---|---|---|---|---|---|---|---|---|---|---|---|---|---|---|
| Met | Tyr | Lys | Asp | Leu | Glu | Gly | Lys | Val | Val | Val | Ile | Thr | Gly | Ser | Ser | |
| 1 | | | | 5 | | | | | 10 | | | | | 15 | | |

| aca | ggt | ttg | gga | aaa | tca | atg | gcg | att | cgt | ttt | gcg | aca | gaa | aaa | gct | 96 |
|---|---|---|---|---|---|---|---|---|---|---|---|---|---|---|---|---|
| Thr | Gly | Leu | Gly | Lys | Ser | Met | Ala | Ile | Arg | Phe | Ala | Thr | Glu | Lys | Ala | |
| | | | 20 | | | | | 25 | | | | | 30 | | | |

| aaa | gta | gtt | gtg | aat | tat | cgt | tct | aag | gaa | gac | gaa | gct | aac | agc | gtt | 144 |
|---|---|---|---|---|---|---|---|---|---|---|---|---|---|---|---|---|
| Lys | Val | Val | Val | Asn | Tyr | Arg | Ser | Lys | Glu | Asp | Glu | Ala | Asn | Ser | Val | |
| | | | 35 | | | | | 40 | | | | | 45 | | | |

| tta | gaa | gaa | att | aaa | aga | gtt | ggc | gga | gag | gct | att | gcc | gtt | aaa | ggt | 192 |
|---|---|---|---|---|---|---|---|---|---|---|---|---|---|---|---|---|
| Leu | Glu | Glu | Ile | Lys | Arg | Val | Gly | Gly | Glu | Ala | Ile | Ala | Val | Lys | Gly | |
| 50 | | | | | 55 | | | | | 60 | | | | | | |

| gac | gta | aca | gtt | gag | tct | gat | gta | atc | aat | tta | gtt | caa | tct | gca | att | 240 |
|---|---|---|---|---|---|---|---|---|---|---|---|---|---|---|---|---|
| Asp | Val | Thr | Val | Glu | Ser | Asp | Val | Ile | Asn | Leu | Val | Gln | Ser | Ala | Ile | |
| 65 | | | | 70 | | | | | 75 | | | | | 80 | | |

| aaa | gaa | ttt | gga | aag | cta | gac | gtt | atg | att | aac | aac | gca | gga | cta | gaa | 288 |
|---|---|---|---|---|---|---|---|---|---|---|---|---|---|---|---|---|
| Lys | Glu | Phe | Gly | Lys | Leu | Asp | Val | Met | Ile | Asn | Asn | Ala | Gly | Leu | Glu | |
| | | | | 85 | | | | | 90 | | | | | 95 | | |

| aat | ccg | gtt | tca | tct | cat | gaa | atg | tct | tta | agc | gat | tgg | aat | aaa | gta | 336 |
|---|---|---|---|---|---|---|---|---|---|---|---|---|---|---|---|---|
| Asn | Pro | Val | Ser | Ser | His | Glu | Met | Ser | Leu | Ser | Asp | Trp | Asn | Lys | Val | |
| | | | 100 | | | | | 105 | | | | | 110 | | | |

| att | gat | acg | aac | tta | acg | gga | gct | ttc | tta | ggt | agt | cgt | gaa | gcg | att | 384 |
|---|---|---|---|---|---|---|---|---|---|---|---|---|---|---|---|---|
| Ile | Asp | Thr | Asn | Leu | Thr | Gly | Ala | Phe | Leu | Gly | Ser | Arg | Glu | Ala | Ile | |
| | | | 115 | | | | | 120 | | | | | 125 | | | |

| aaa | tat | ttt | gtt | gaa | aat | gat | att | aag | gga | aca | gtt | att | aac | atg | tcg | 432 |
|---|---|---|---|---|---|---|---|---|---|---|---|---|---|---|---|---|
| Lys | Tyr | Phe | Val | Glu | Asn | Asp | Ile | Lys | Gly | Thr | Val | Ile | Asn | Met | Ser | |
| 130 | | | | | 135 | | | | | 140 | | | | | | |

| agt | gtt | cac | gag | aaa | att | cct | tgg | cca | tta | ttt | gtt | cat | tat | gca | gca | 480 |
|---|---|---|---|---|---|---|---|---|---|---|---|---|---|---|---|---|
| Ser | Val | His | Glu | Lys | Ile | Pro | Trp | Pro | Leu | Phe | Val | His | Tyr | Ala | Ala | |
| 145 | | | | 150 | | | | | 155 | | | | | 160 | | |

| agt | aaa | ggc | ggt | atg | aag | ctt | atg | act | gaa | aca | ctg | gca | tta | gaa | tac | 528 |
|---|---|---|---|---|---|---|---|---|---|---|---|---|---|---|---|---|
| Ser | Lys | Gly | Gly | Met | Lys | Leu | Met | Thr | Glu | Thr | Leu | Ala | Leu | Glu | Tyr | |
| | | | | 165 | | | | | 170 | | | | | 175 | | |

| gct | cca | aaa | ggt | att | cgt | gta | aat | aac | att | gga | ccg | gga | gcg | att | aat | 576 |
|---|---|---|---|---|---|---|---|---|---|---|---|---|---|---|---|---|
| Ala | Pro | Lys | Gly | Ile | Arg | Val | Asn | Asn | Ile | Gly | Pro | Gly | Ala | Ile | Asn | |
| | | | 180 | | | | | 185 | | | | | 190 | | | |

| aca | ccg | att | aac | gct | gag | aaa | ttt | gct | gat | cct | gag | cag | cgt | gca | gat | 624 |
|---|---|---|---|---|---|---|---|---|---|---|---|---|---|---|---|---|
| Thr | Pro | Ile | Asn | Ala | Glu | Lys | Phe | Ala | Asp | Pro | Glu | Gln | Arg | Ala | Asp | |
| | | | 195 | | | | | 200 | | | | | 205 | | | |

| gta | gaa | agc | atg | att | cca | atg | gga | tac | atc | gga | gag | ccg | gaa | gaa | att | 672 |
|---|---|---|---|---|---|---|---|---|---|---|---|---|---|---|---|---|
| Val | Glu | Ser | Met | Ile | Pro | Met | Gly | Tyr | Ile | Gly | Glu | Pro | Glu | Glu | Ile | |
| 210 | | | | | 215 | | | | | 220 | | | | | | |

| gca | gca | gtt | gct | gca | tgg | cta | gct | tct | tca | gag | gcg | agt | tat | gta | aca | 720 |
|---|---|---|---|---|---|---|---|---|---|---|---|---|---|---|---|---|
| Ala | Ala | Val | Ala | Ala | Trp | Leu | Ala | Ser | Ser | Glu | Ala | Ser | Tyr | Val | Thr | |
| 225 | | | | 230 | | | | | 235 | | | | | 240 | | |

| gga | att | acg | ctc | ttt | gct | gac | ggc | ggt | atg | aca | ctg | tac | cca | tca | ttc | 768 |
|---|---|---|---|---|---|---|---|---|---|---|---|---|---|---|---|---|
| Gly | Ile | Thr | Leu | Phe | Ala | Asp | Gly | Gly | Met | Thr | Leu | Tyr | Pro | Ser | Phe | |

```
                        245                 250                 255
caa gca gga cgc gga taa                                                         786
Gln Ala Gly Arg Gly
        260

<210> SEQ ID NO 14
<211> LENGTH: 261
<212> TYPE: PRT
<213> ORGANISM: Bacillus megaterium

<400> SEQUENCE: 14

Met Tyr Lys Asp Leu Glu Gly Lys Val Val Ile Thr Gly Ser Ser
1               5                   10                  15

Thr Gly Leu Gly Lys Ser Met Ala Ile Arg Phe Ala Thr Glu Lys Ala
            20                  25                  30

Lys Val Val Asn Tyr Arg Ser Lys Glu Asp Glu Ala Asn Ser Val
        35                  40                  45

Leu Glu Glu Ile Lys Arg Val Gly Gly Glu Ala Ile Ala Val Lys Gly
        50                  55                  60

Asp Val Thr Val Glu Ser Asp Val Ile Asn Leu Val Gln Ser Ala Ile
65                  70                  75                  80

Lys Glu Phe Gly Lys Leu Asp Val Met Ile Asn Asn Ala Gly Leu Glu
                85                  90                  95

Asn Pro Val Ser Ser His Glu Met Ser Leu Ser Asp Trp Asn Lys Val
            100                 105                 110

Ile Asp Thr Asn Leu Thr Gly Ala Phe Leu Gly Ser Arg Glu Ala Ile
        115                 120                 125

Lys Tyr Phe Val Glu Asn Asp Ile Lys Gly Thr Val Ile Asn Met Ser
        130                 135                 140

Ser Val His Glu Lys Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Glu Gln Arg Ala Asp
        195                 200                 205

Val Glu Ser Met Ile Pro Met Gly Tyr Ile Gly Glu Pro Glu Glu Ile
        210                 215                 220

Ala Ala Val Ala Ala Trp Leu Ala Ser Ser Glu Ala Ser Tyr Val Thr
225                 230                 235                 240

Gly Ile Thr Leu Phe Ala Asp Gly Gly Met Thr Leu Tyr Pro Ser Phe
                245                 250                 255

Gln Ala Gly Arg Gly
        260
```

CANDIDA CARBONYL REDUCTASE AND METHOD FOR PREPARING (R)-LIPOIC ACID PRECURSOR

RELATED APPLICATIONS

This application is the National Stage of International Patent Application No. PCT/CN2015/073615, filed Mar. 4, 2015, which is hereby incorporated by reference in its entirety.

SEQUENCE LISTING

The sequences listed in the accompanying Sequence Listing are presented in accordance with 37 C.F.R. 1.822. The Sequence Listing is submitted as an ASCII computer readable text file, which is incorporated by reference herein.

FIELD OF THE INVENTION

The patent application relates to the field of bio-engineering technology, in particular, to *Candida parapsilosis* and the carbonyl reductase expressed therefrom, the encoding gene and amino acid sequence of the enzyme, and recombinant expression vectors and recombinant expression transformants containing said encoding genes, use of said carbonyl reductase or recombinant expression transformant as catalysts in the asymmetric reduction of prochiral carbonyl compounds, such as reduction of 6-carbonyl-8-chlorocaprylate to producte optically pure (R)-6-hydroxyl-8-chlorocaprylate.

BACKGROUND OF THE INVENTION

Since Reed isolated α-lipoic acid from pork liver for the first time in 1950, the study of the physiological activity thereof deepens. α-lipoic acid belongs to vitamin drugs and is both lipid-soluble and water-soluble antioxidant, which can eliminate pathogenic radicals in vivo. It has been reported that α-lipoic acid can be used to treat radioactive damage, or diseases such as liver dysfunction and subacute necrotizing encephalomyelopathy. In China, α-lipoic acid is mainly used in the treatment of liver diseases such as acute hepatitis, hepatocirrhosis, and fatty liver. The physiological activity of α-lipoic acid is only limited to d-lipoic acid (i.e. (R)-α-lipoic acid), while (S)-α-lipoic acid substantially lacks physiological activities and other side-effects. Commercial optically pure (R)-α-lipoic acid is replacing racemic lipoic acid.

Current synthesis methods of (R)-α-lipoic acid are classified into chemical methods and biological ones. Elliott et al. conducted asymmetric synthesis of (R)-α-lipoic acid with a total yield of 37% by induction with chiral auxiliary reagents, but its strict reaction conditions and high cost of the reagents used limited its use in industry (Tetrahedron Letters, 1985, 26 (21): 2535-2538). Gopalan attempted to generate (R)-α-lipoic acid by catalysis with microbial enzymes, but the total yield was only 10% and the practicability thereof was poor (Journal of the Chemical Society, Perkin Trans., 1990, 7: 1897-1900). Recently, one of the well studied synthesis methods is enantio-separation which seperates racemic lipoic acid or its precursors with chiral resolving agents or esterases/lipases and converts them into (R)-α-lipoic acid. However, as (S)-α-lipoic acid is generated in the process at the same time, the theoretical highest yield is only 50%.

Alternatively, preparation of (R)-6-hydroxy-8-chlorocaprylate by enzymatic reduction is getting attention, but the yield and optical purity of the product thereof is not good in a few reports currently. For example, Olbrich et al. utilized the whole cell of *Geotrichum candidum* to catalyze the asymmetric reduction of 6-carbonyl-8-chlorocaprylate to generate (R)-6-hydroxy-8-chlorocaprylate, with a substrate concentration of 5 g/L, and after reaction for 24 h, the yield was only 62% and the ee value of the product was 88% (U.S. Pat. No. 7,135,328 B2). Müller et al. utilized the alcohol dehydrogenase TbADH from *Thermoanaerobium brokii* to catalyze the reductive conversion of 2 g/L of 6-carbonyl-8-chlorocaprylate to produce (R)-6-hydroxy-8-chlorocaprylate with an optical purity of 99.5%, but its conversion rate was only 85%, and it was necessary to add 0.5 mM coenzyme and 1 mM dithiothreitol (DTT) in the reaction system (U.S. Pat. No. 7,157,253 B2). Werner et al. utilized NgADH from *Nocardia globulera* to prepare (R)-6-hydroxy-8-chlorocaprylate, and the concentration of the substrate could be 44 g/L, but the ee value of the product thereof was not disclosed (WO 2007/028729 A1, 2007). Gupta et al. utilized an oxidoreductase from *Metschnikowia zobellii* to convert 85 g/L of the substrate 6-carbonyl-8-chlorocaprylate into the product (R)-6-hydroxy-8-chlorocaprylate, and it was necessary to add 0.1 mM coenzyme into the reaction system and the conversion rate after 24 h was only 55%, though the ee value of the product could get 97% (WO 2005049816 A2). To sum up, existing biological catalysts and their technical levels are far away from industrial application. For example, the carbonyl reductases reported so far generally have technical problems such as low catalytic activity, poor substrate tolerance, long reaction time, and undesired optical purity.

It can be seen that current synthesis methods of (R)-α-lipoic acid have various defects and are not able to meet the increasing demandment of optically pure (R)-α-lipoic acid. Therefore, there is still a need for improved synthesis methods of (R)-α-lipoic acid which meet the industrial requirement with high efficiency and low cost.

SUMMARY OF THE INVENTION

With respect to the deficiencies in the prior art, the inventor provides *Candida parapsilosis* CGMCC 9630. The carbonyl reductases expressed by such strain have advantages such as capable of working with a catalytic substrate in high concentration, mild reaction conditions, environmental friendship, high yield, and high optical purity of the product.

The carbonyl reductase CpKR expressed by said *Candida parapsilosis* CGMCC 9630, its encoding gene, a recombinant vectors and a recombinant transformant expressing said carbonyl reductase, use of said strain or carbonyl reductase in catalytic asymmetric reduction of prochiral carbonyl compounds, and method of preparing chiral secondary alcohols, particularly (R)-6-hydroxy-8-chlorocaprylate is disclosed herein. The carbonyl reductase has very high catalytic activity, stereoselectivity and substrate tolerance.

In another aspect, the inventor provides a new carbonyl reductase, and the amino acid sequence thereof is set forth in SEQ ID No. 2 in sequence listing. The method of preparing the carbonyl reductase CpKR comprises but not limited to: 1) obtaining the carbonyl reductase by direct extracting and isolating from the cells of *Candida parapsilosis* CGMCC 9630; or 2) obtaining the carbonyl reductase by heterologous recombination expression of the gene encoding the carbonyl reductase with common technical means in the art.

In another aspect, the inventor provides the gene encoding the carbonyl reductase, the recombinant expression vectors and recombinant expression transformant containing said gene. The inventor also provides the method of preparing the carbonyl reductase, comprising the step of cultivating said *Candida parapsilosis* or a host cell that contains the recombination expression vector of said carbonyl reductase gene.

Correspondingly, there is also provided use of the culture of *Candida parapsilosis* CGMCC 9630 or related recombination expression vector thereof or the resulted carbonyl reductase in asymmetric reduction of a prochiral carbonyl compound, wherein the prochiral carbonyl compound can be selected from the following formula:

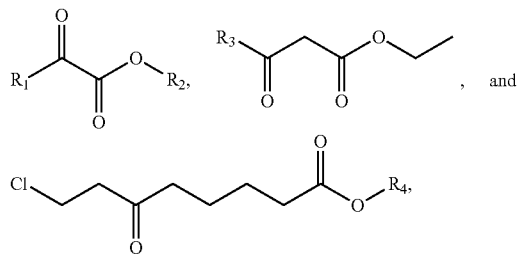

wherein $R_1$ is selected from —$CH_2(CH_3)_2$, -2-Cl—$C_6H_4$ and —$(CH_2)_2C_6H_5$; $R_2$ is —$CH_3$ or —$CH_2CH_3$; $R_3$ is —$CH_2Cl$, —$CH_2CH_3$ or —$(CH_2)_2CH_3$; $R_4$ is —$CH_3$ or —$CH_2CH_3$, and particularly, the prochiral carbonyl compound is ethyl 6-carbonyl-8-chlorocaprylate.

Particularly, when the prochiral carbonyl compound is ethyl 6-carbonyl-8-chlorocaprylate, thereby (R)-α-lipoic acid can be obtained. A representation of a useful reaction scheme is showed as follows:

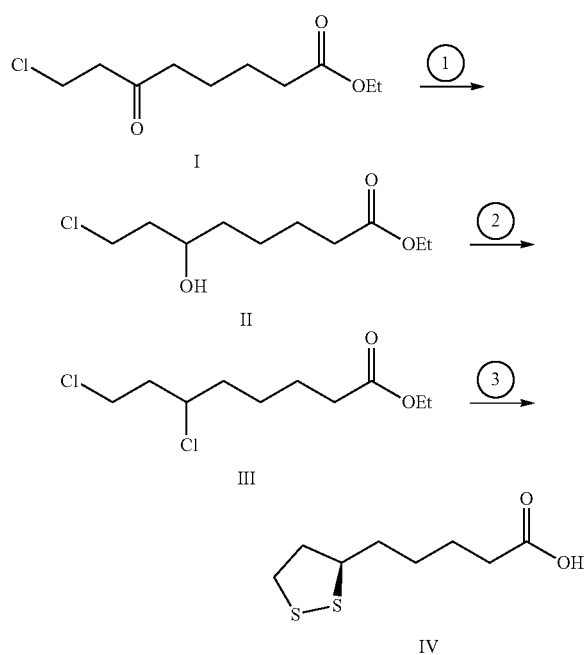

wherein, formula (I) is ethyl 6-carbonyl-8-chlorocaprylate; formula (II) is ethyl (R)-6-hydroxy-8-chlorocaprylate; formula (III) is ethyl (R)-6,8-dichlorocaprylate; formula (IV) is (R)-α-lipoic acid. In each step, ① is carbonyl reductase; such reaction needs to be conducted in the presence of NADPH; the carbonyl substrate is catalytically reduced while NADPH is oxidized into corresponding oxidized coenzyme $NADP^+$; ② is $SOCl_2$; ③ is $Na_2S$ added with S. In one embodiment, the disclosure relates to particularly providing active carbonyl reductase with the culture of CGMCC 9630 cells or related recombinant transformant in step ①, generating (R)-6-hydroxy-8-chlorocaprylate by asymmetric reduction of ethyl 6-carbonyl-8-chlorocaprylate, for synthesizing (R)-α-lipoic acid.

In above uses, the concentration of the prochiral carbonyl compound can be from 1 to 1500 mmol/L; optionally the amount of said carbonyl reductase is from 8.0 to 800 U/mmol prochiral carbonyl compound. The NADPH required in the reaction can be provided with cell culture or added additionally as catalyst, and when appropriate, the amount of the added coenzyme NADPH can be 0 to 10 mmol/L. Alternatively, NADPH is provided indirectly by adding glucose dehydrogenase, glucose and $NADP^+$, and when appropriate, the amount of glucose dehydrogenase can be from 0 to 340 U/mmol prochiral carbonyl compound, the amount of glucose can be from 0 to 0.3 g/mmol prochiral carbonyl compound, and the added amount of $NADP^+$ can be from 0 to 1.0 mmol/L.

In one embodiment, enzymetic reduction of 6-carbonyl-8-chlorocaprylate is conducted by above scheme, and (R)-6-hydroxy-8-chlorocaprylate in a single configuration is generated asymmetrically, thereby synthesizing (R)-α-lipoic acid. In comparison with prior art, the method have several advantages such as capable of working with a catalytic substrate in a high concentration, mild reaction conditions, environmental friendship, high yield, and high optical purity of the product. The theoretical yield thereof can be up to 100%.

DESCRIPTION OF THE INVENTION

Figure 1:
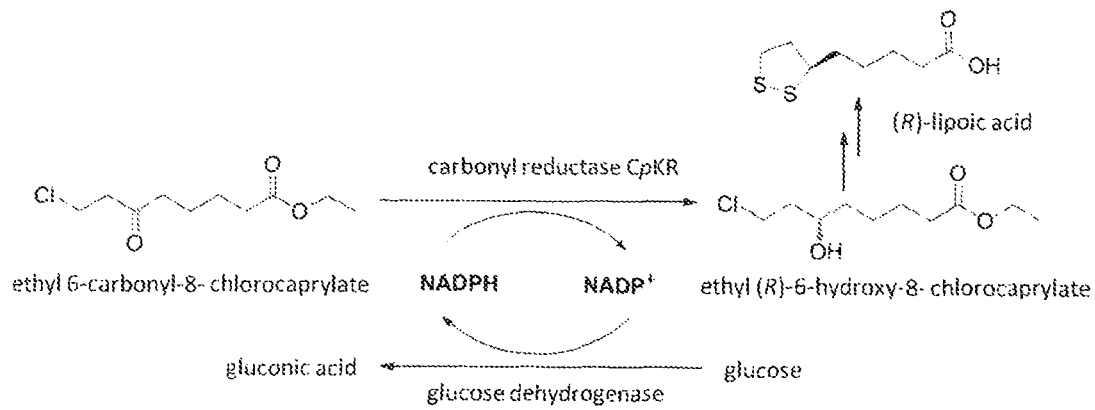
FIG. 1 is the representation of catalytic synthesis of ethyl (R)-6-hydroxy-8-chlorocaprylate with carbonyl reductase CgKR.

Disclosed herein is *Candida parapsilosis* CGMCC 9630. Such strain is originally designated as ECU 6481, which is isolated in East China University of Science and Technology in Fengxian and identified as *Candida parapsilosis* by classification experiments and 16S rDNA analysis. When screening with the strains preserved in the research group for reduction activity with ethyl 6-carbonyl-8-chlorocaprylate as a substrate, we found the resting cells of said strain can catalyze asymmetric reduction of ethyl 6-carbonyl-8-chlorocaprylate to produce ethyl (R)-6-hydroxy-8-chlorocaprylate, and the ee value of the produce was 97%. Such strain has been deposited on Sep. 1, 2014 in China General Microbiological Culture Collection Center with the deposit number CGMCC 9630.

Based on the obtained *Candida parapsilosis* CGMCC 9630 with high activity and stereoselectivity after screening, in combination with common technical means in the art, the inventor designed primers to conduct molecular cloning based on the sequences derived from *Candida parapsilosis* and predicted as carbonyl reductase associated sequences available in NCBI database, and the obtained fragments were recombinantly expressed in *E. coli*. The recombinantly expressed carbonyl reductase was used to catalyze the reduction of ethyl 6-carbonyl-8-chlorocaprylate, and the catalytic activity and the ee value of the reduced product were determined. The ee value of the final product was 97%, and the carbonyl reductase with the highest enzymatic reductive activity was CpKR, which has an amino acid sequence as set forth in SEQ ID No. 2. Based on that, the mutants with amino acid sequences as set forth in SEQ ID Nos.4 and 6 were obtained by replacing one or more amino acid residues in the amino acid sequence SEQ ID No.2, with the provision that the enzymatic activity thereof was maintained.

The carbonyl reductase CpKR and the mutants thereof can be encoded by the nucleic acid sequences as set forth in SEQ ID Nos. 1, 3 and 5. Based on the disclosed amino acid sequence of the carbonyl reductase, it is not difficult to prepare the encoding gene of the carbonyl reductase (CpKR) of the disclosure with common technical means in the art. The nucleic acid molecule containing said encoding gene includes but not limited to: a CpKR-encoding nucleic acid molecule naturally generated and extracted from an organism, or a CpKR-encoding nucleic acid molecule obtained by engineering of an existing nucleic acid fragment with gene cloning, or a CpKR enzyme-encoding nucleic acid molecule obtained by artificial synthesis. Term "nucleic acid" and "nucleic acid molecule" as used herein can be interchanged and refer to deoxynucleoside or nucleoside in single chain or double chain and a polymer thereof.

A skilled person in the art knows that because of the degeneracy of codon, the nucleic acid molecule encoding the carbonyl reductase (amino acid sequences as set forth in SEQ ID Nos. 2, 4 and 6 in sequence listing) is not limited to the nucleic acid sequences as set forth in SEQ ID Nos. 1, 3 and 5, but also includes the homologues of a nucleic acid molecule obtained by introducing replacement, as long as that the nucleic acid molecule encodes the protein having the amino acid sequence as set forth in SEQ ID Nos. 2, 4 and 6.

The nucleic acid molecule encoding the carbonyl reductase of the disclosure is preferably derived from: with the genomic DNA of *Candida parapsilosis* CGMCC 9630 as a template, obtaining the entire nucleic acid molecule encoding the carbonyl reductase with common technical means in the art such as polymerase chain reaction (PCR), wherein the related synthetic primers are preferably set forth in SEQ ID No. 7 and SEQ ID No. 8:

```
Forward primer SEQ ID No. 7:
CCGGAATTCATGACAGTATTTGTCTCAGGTGCA

Reverse primer SEQ ID No. 8:
CCGCTCGAGTTACTTGGCATCGAGAAGTTGTTT
```

Wherein, the EcoRI restriction site is underlined in the forward primer, and the XhoI restriction site is underlined in the reverse primer.

Figure 2:
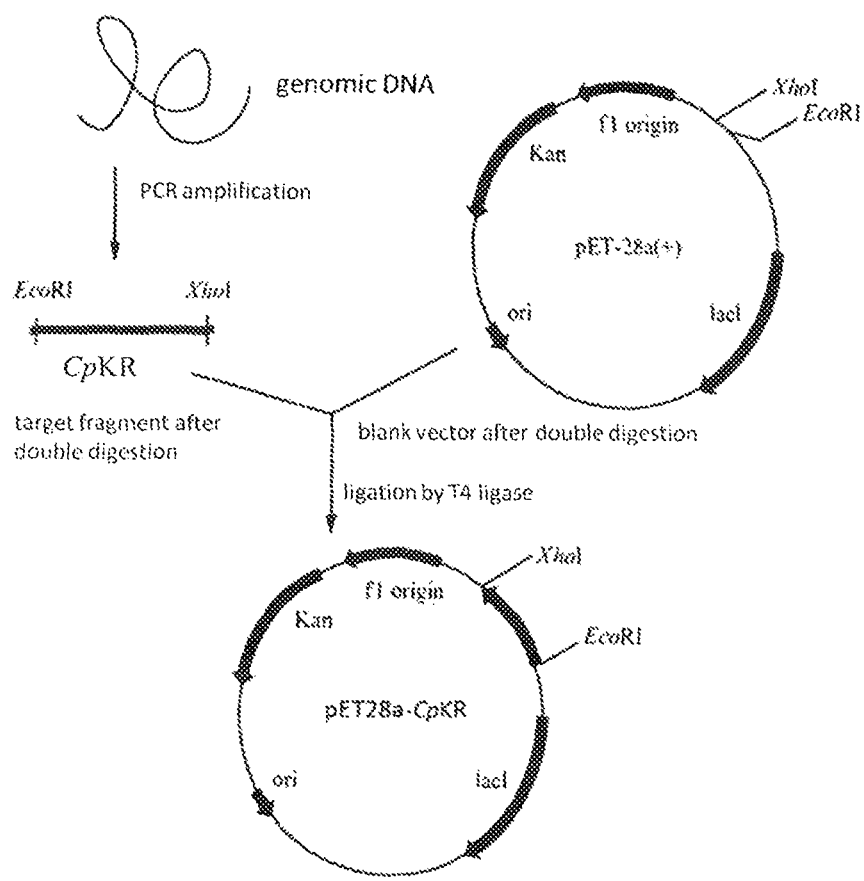
FIG. 2 is the representation of the construction of plasmid pET28a-CpKR.

Also disclosed herein is a recombinant expression vector containing the gene of carbonyl reductase. Term "expression vector" refers to a vector, plasmid or vehicle that can be designed for inserting and expressing a nucleic acid sequence. The expression vector can provide regulatory sequences for transcription and translation for inducible or constitutive expression, wherein the encoding region is operably placed in the transcription initiation region (e.g., a promoter or enhancer) and under the transcription control of transcription and translation termination regions. Said expression vector can be a conventional vector in the art, such as commercial plasmid, cosmid, phage or virus vector. The recombinant expression vector can be constructed by introducing the nucleotide sequence encoding the carbonyl reductase into various expression vectors by common technical means in the art. The vector of the disclosure is preferably plasmid pET-28a. The nucleic acid product and expression vector pET-28a obtained by PCR amplification can undergo double digestion with restriction enzymes such as EcoRI and XhoI respectively, forming complementary sticky ends, before being linked with ligase such as T4 DNA ligase to form the recombinant expression vector containing the carbonyl reductase CpKR encoding gene of the disclosure, such as pET28a-CpKR (the plasmid representation is seen in FIG. 2).

Also disclosed herein is a recombinant expression transformant containing the carbonyl reductase gene or the recombinant expression vector thereof. The recombinant expression transformant can be prepared by transferring the recombinant expression vector of the disclosure into a host cell. The host cell of the disclosure is preferably a common host micro-organism in the art, with the provision that the recombinant expression vector can self-replicate stably and express the carbonyl reductase gene effectively. The host cell is preferably *E. coli*, more preferably *E. coli* BL21 (DE3) or *E. coli* DH 5a. In the description herein, terms "recombinant micro-organism", "recombinant cell" and "recombinant host cell" are interchanged and refer to those that undergoes genetic modification to replicate and express or overexpress an endogenous polynucleotide or express a non-endogenous sequence such as the sequence contained in a vector, including the progeny thereof.

Also disclosed herein is a method of preparing the recombinant carbonyl reductase. The carbonyl reductase CpKR with asymmetric reduction activity of catalyzing 6-carbonyl-8-chlorocaprylate can be obtained by culturing above recombinant expression transformant. The used culture medium can be selected from conventional culture mediums in the art, such as LB culture medium (peptone 10 g/L, yeast extract 5 g/L, NaCl 10 g/L, pH 7.0) and the like. The culture of transformant can refer to common operation in the art. For example, in the embodiment that the contained expression vector provides inducible expression, the culture condition of the recombinant expression transformant can be: culturing at 37° C. to $OD_{600}$ of about 0.6 and adding isopropyl-β-D-thiogalacto-pyranoside (IPTG) to induce, the concentration of the inducer is optionally from 0.05 to 1.0 mmol/L (e.g. 0.2 mmol/L), and the induction temperature is optionally from 16 to 25° C. (e.g., 20° C.), and the induction can last for from 12 to 24 h (e.g., 16 h). Above carbonyl reductase can be expressed effectively by culturing the recombinant expression transformant of the disclosure in a suitable culture medium and under appropriate conditions and inducing with suitable agents and conditions as desired.

In the asymmetric reduction of the disclosure, the pellet precipitation obtained by culturing *Candida parapsilosis* CGMCC 9630 or the corresponding recombinant reansformant is used as catalyst, and the obtained pellet precipitation is optionally lyophilized for long storage for subsequent use. Another advantage of asymmetric reduction with the pellet is that the coenzyme NADPH required for CpKR catalytic reaction is also provided in addition to the catalyst, which eliminates the addition of expensive reductive coenzyme and helps to reduce the cost of reaction.

Similarly, in order to control cost, oxidative coenzyme NADP$^+$ can also be added to the reaction system, while auxiliary glucose dehydrogenase and cheap co-substrate glucose are added simultaneously to provide NADPH necessary for CpKR reaction by generating NADPH from catalyzing the reduction of NADP$^+$. The auxiliary glucose dehydrogenase can be added directly as an active protein. The auxiliary glucose dehydrogenase can be provided as recombinant product in same or different host cell with CpKR, which means that CpKR and glucose dehydrogenase can be expressed from two host cells respectively, or from the same or different expression vectors in a same host cell. The co-expression of these two enzymes allows simplified fermentation production process, simplified reaction system, reduced amount of biological catalyst, and increased reduction and regeneration efficiency of coenzyme NADP$^+$. Therefore, also disclosed herein is a method of co-expressing the carbonyl reductase CpKR and glucose dehydrogenase. The amino acid sequence of the glucose dehydrogenase can be set forth in SEQ ID No. 14, which can be encoded by the nucleotide sequence as set forth in SEQ ID No. 13.

In one embodiment, two host cells can be used to express the carbonyl reductase CpKR and glucose dehydrogenase respectively, and then the obtained cells can be used in catalytic reaction in proper ratio as desired. In another embodiment, the carbonyl reductase CpKR and glucose dehydrogenase can be expressed with two different vectors respectively in the same host cell, and then the obtained cells are used in catalytic reaction. In another embodiment, the carbonyl reductase CpKR-encoding and glucose dehydrogenase-encoding sequences can be inserted into the same expression vector, introduced into a host cell, and then the obtained cells can be used in catalytic reaction.

These recombinantly transformed host cells can be obtained with common technical means. For example, the encoding nucleic acids of the carbonyl reductase CpKR and glucose dehydrogenase can be linked into two different expression plasmids respectively, and transferred into a host cell simultaneously. Alternatively, when using a single expression vector, the encoding nucleic acids of the carbonyl reductase CpKR and glucose dehydrogenase can be linked into the expression plasmid in any order, and then transferred into a host cell. The glucose dehydrogenase can be derived from BmGDH of *Bacillus megaterium*; the expression plasmid can be pET28a; and the host cell can be *E. coli* BL21 (DE3).

The carbonyl reductase can be isolated by the following process: corresponding recombinant expression transformant cells, after centrifugation, are resuspended in 100 mM Tris-HCl buffer, pH 7.0, ultrasonicated and broken in ice bath (e.g., with a working power of 400 W for 4 s, pause for 6 s for 99 cycles), then the cell debris is precipitated by centrifugation (e.g., centrifugation at 4° C., 12000 rpm for 10 minutes), and the supernatant is collected as the crude enzyme solution of the recombinant carbonyl reductase CpKR. The recombinantly expressed glucose dehydrogenase can be isolated and purified according to reference documents, see, e.g., *Journal of Industrial Microbiology and Biotechnology* 2011, 38, 633-641.

In order to achieve above co-expression, suitable primers can be used to amplify and obtain the encoding sequences of the carbonyl reductase CpKR and glucose dehydrogenase. For example, the encoding sequence of the carbonyl reductase CpKR as set forth in SEQ ID No. 1 can be obtained with the following SEQ ID Nos. 9 and 10 as primers, and the encoding sequence of the glucose dehydrogenase as set forth in SEQ ID No. 13 can be obtained with the following SEQ ID Nos. 11 and 12 as primers.

```
CpKR-NdeI, SEQ ID No. 9:
GGAATTCCATATGACAGTATTTGTCTCAGGTGC

CpKR-EcoRI, SEQ ID No. 10:
CCGGAATTCTTACTTGGCATCGAGAAGTTGTTT

BmGDH-SalI, SEQ ID No. 11:
ACGCGTCGACAAGGAGATATAATGTATAAAGATTTAGAAGG

BmGDH-XhoI, SEQ ID No. 12:
CCGCTCGAGTTATCCGCGTCCTGCTTGGAAT
```

In above sequences, the restriction site in each primer is underlined, respectively.

The activity of the carbonyl reductase can be determined with the following process: 1 mL reaction system (100 mmol/L Tris-HCl buffer, pH 7.0) containing 2 mmol/L ethyl 6-carbonyl-8-chlorocaprylate and 0.1 mmol/L NADPH is preheated to 30° C., then a suitable amount of carbonyl reductase is added, the reaction is conducted under 30° C., and the absorbance change of NADPH at 340 nm is detected in a spectrophotometer, and the absorbance change within 1 minute is recorded.

The activity of the glucose dehydrogenase can be determined with the following process: 1 mL reaction system (100 mmol/L Tris-HCl buffer, pH 7.0) containing 10 mmol/L glucose, 1 mmol/L NADP$^+$ is preheated to 30° C., then a suitable amount of glucose dehydrogenase is added. At 30° C., the reaction is carried out in a cuvette of a spectrophotometer, and the absorbance change of NADPH at 340 nm is detected in situ, and the absorbance change within 1 minute is recorded.

When determining the activities of the carbonyl reductase and glucose dehydrogenase, enzyme activity can be calculated according to the following formula:

$$\text{enzyme activity } (U) = EW \times V \times 10^3 / (6220 \times 1)$$

wherein, EW is absorbance change at 340 nm within 1 minute; V is the volume of reaction solution in ml; 6220 is the molar extinction coefficient of NADPH in L/(mol·cm); and 1 is optical path distance in cm. With respect to the carbonyl reductase, one activity unit corresponds to the amount of enzyme necessary for oxidation of 1 μmol NADPH per minute under above conditions. With respect to the glucose dehydrogenase, one activity unit corresponds to the amount of enzyme necessary for reduction of 1 μmol NADP$^+$ per minute under above conditions.

Also disclosed herein is use of the carbonyl reductase CpKR in catalytic reduction of prochiral carbonyl compounds to generate optically pure secondary alcohols. The use comprises: the carbonyl reductase or recombinant expression transformant is used as catalyst, the prochiral carbonyl compounds to be converted, glucose and glucose dehydrogenase (if desired) are added to a buffer at pH 6.0 to 7.5 (e.g., pH 7.0), after biological conversion for a particular duration, and optically pure chiral hydroxyl compounds are generated, for example, (R)-6-hydroxy-8-chlorocaprylate, the synthetic precursor of (R)-lipoic acid.

The used buffer of the disclosure is a common buffer in the art. In one embodiment, the buffer is Tris-HCl buffer, pH 7.0, and other buffers include sodium phosphate buffer and potassium phosphate buffer, with the provision that the buffering range thereof is pH 6.0 to 7.5. The concentration range of a buffer can be 10 to 200 mM, preferably 50 to 100 mM.

When referring to compounds, term "chemically pure" means a purified product, wherein the compound accounts for 85% or more (e.g., 90%, 95% or more) of the total amount, compared with the undesired impurities. When referring to the chiral compounds such as the precursor of lipoic acid, term "optically pure" means a purified product, wherein the (R)-enantiomer accounts for 96.5% or more (e.g., 97%, 97.5%, 98%, 98.5%, 99% or more) of the total enantiomers compared with the undesired (S)-enantiomer. In the disclosure, optical purity is generally indicated as term "enantiomeric excess" or symbol "ee", which refers to the excess amount of an enantiomer in a mixture compared with another enantiomer, such as the excess amount of (R) in the precursor compounds of lipoic acid compared with (S). Unless otherwise noted, when referring to purity or ee value in the description, ">99%" means that the content of a residual substrate or a certain enantiomer is lower than the low limit of detection and cannot be accurately determined. Herein, analysis of ee value can be performed by passing the acetylated products through gas chromatography (e.g., using CP-Chirasil-DEX CB column), and an exemplary condition for gas chromatography is: using nitrogen as the carrier gas, a inlet temperature of 280° C., a detector temperature of 280° C., and a column temperature of 160° C.

Term "prochiral carbonyl compound" is a class of keto ester compounds, ester compounds containing carbonyl substituent in the back bone, wherein such compounds are not chiral natively and produce chiral hydroxyl esters after catalytic asymmetric reduction. For example, said prochiral carbonyl compound can be selected from the following formula:

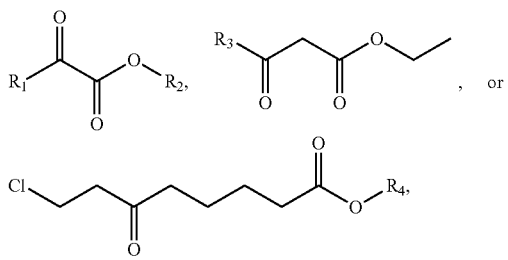

wherein,
$R_1$ is selected from —$CH_2(CH_3)_2$, -2-Cl—$C_6H_4$ or —$(CH_2)_2C_6H_5$;
$R_2$ is —$CH_3$ or —$CH_2CH_3$;
$R_3$ is —$CH_2Cl$, —$CH_2CH_3$ or —$(CH_2)_2CH_3$;
$R_4$ is —$CH_3$ or —$CH_2CH_3$.

The asymmetric reduction is preferably conducted under proper oscillation and mixing. Reaction temperature can be from 20 to 30° C., substrate concentration can optionally be from 1 to 1500 mmol/L, amount of carbonyl reductase can optionally be from 8.0 to 800 U enzyme/mmol substrate; amount of glucose dehydrogenase can optionally be from 0 to 340 U enzyme/mmol substrate; amount of glucose can optionally be from 0 to 0.3 g/mmol substrate; amount of additional added coenzyme $NADP^+$ can optionally be from 0 to 0.1 mmol/L; amount of additional added coenzyme NADPH can optionally be from 0 to 10 mmol/L. During the reaction, conversion rate is determined by intermittent sampling, and reaction time is determined when conversion rate achieves 99% or more and usually 2 to 12 h. Conversion rate can be analyzed by gas chromatography, for example, using Rxi®-5Sil MS chromatographic column, nitrogen as the carrier gas, an inlet temperature of 280° C., a detector temperature is 280° C., and a column temperature is 160° C.

When the asymmetric reduction is ended, the reaction solution is extracted with equal amount of water-insoluble organic solvents such as ethyl acetate, butyl acetate, toluene, dichloromethane, trichloromethane, isopropyl ether, and methyl ter-butyl ether, and the extraction is repeated twice. The extract is combined and dried by adding anhydrous sodium sulfate overnight. Solvent is removed through rotary evaporation and the crude extract of optically pure product is obtained. The crude extract is further purified through common technical means such as distillation under reduced pressure to obtain a highly chemically and optically pure product.

The *Candida parapsilosis* CGMCC 9630 strain and the carbonyl reductase CpKR synthesized by the same provided herein can be used to efficiently catalyze the asymmetric reduction of 6-carbonyl-8-chlorocaprylate, and generate optically pure (R)-6-hydroxy-8-chlorocaprylate. Using such enzymic catalytic technology, substrate concentration is 1.5 mol/L (or 330 g/L), with a conversion rate of more than 99%, and an ee value of the product of more than 97%. In comparison of other preparation methods for asymmetric reduction of synthetic precursors of (R)-α-lipoic acid, the disclosure has higher concentration and optical purity of product, and is beneficial to achieve production of (R)-α-lipoic acid with high efficiency and low cost, and has the prospect of industrial application.

Above reaction or detection conditions can be combined or modified according to common knowledge in the art, or may be verified through experimentation. The following examples illustrate exemplary embodiments of the disclosure, to help a skilled person in the art understand other objects, features, advantages and various aspects of the disclosure. It should be understood that though the preferable embodiments of the disclosure is described, but the following description and examples are provided for illustration only and are not limiting. The invention is defined by the appended claims.

DESCRIPTION OF EMBODIMENT

Unless otherwise indicated, the specific experiments in the following examples are conducted according to common methods and conditions in the art, or the manufacturer's instructions.

The origin of the materials in the following examples is:
*Candida parapsilosis* CGMCC 9630
Expression plasmid pET28a is available from Novagen.
*E. coli* DH5α and *E. coli* BL21 (DE3) competent cells, 2×Taq PCR MasterMix, agarose gel DNA Recovery Kit are available from Tiangen (Beijing).
Restriction endonucleases EcoR I and Xho I are available from Takara.

Example 1 Culturing of *Candida parapsilosis* CGMCC 9630

*Candida parapsilosis* CGMCC 9630 was inoculated in a culture media (yeast extract 3 g/L, malt extract 3 g/L, soybean peptone 5 g/L, glucose 10 g/L), and cultured at 30° C. for 1 day. After centrifugation of culture liquid at 8000 rpm, the pellet was collected. The collected pellet precipitate was used immediately or stored in a fridge at 4° C. for use within 3 days.

Example 2 Candida parapsilosis Cells Catalyze Reduction of ethyl 6-carbonyl-8-chlorocaprylate 0.2 g pellet precipitate in Example 1 was obtained, and resuspended with 2 mL Tris-HCl buffer (100 mmol/L, pH 7.0), added with 1 mM ethyl 6-carbonyl-8-chlorocaprylate, and placed on a constant temperature mixing apparatus for reaction at 30° C. and 1000 rpm for 12 h. After extraction with equal amount of ethyl acetate, the extract was dried with anhydrous sodium sulfate for more than 6 h. After acetylization of the products, through gas chromatography, the optical purity thereof was determined as 97% ee (R).

Example 3 Gene Cloning of Carbonyl Reductase CpKR

According to the open reading frame of carbonyl reductase CpKR, the upstream primer and downstream primer were designed as follows:

```
Upstream primer SEQ ID No. 7:
CCGGAATTCATGACAGTATTTGTCTCAGGTGCA

Downstream primer SEQ ID No. 8:
CCGCTCGAGTTACTTGGCATCGAGAAGTTGTTT
``` wherein, the underlined portion in the upstream primer is EcoRI restriction site, and the underlined portion in the downstream primer is XhoI restriction site.

PCR amplification was performed with the genomic DNA of Candida parapsilosis CGMCC 9630 as the template. PCR system was: 2×Taq PCR MasterMix 25 μl, upstream primer and downstream primer (10 ng/μl) each 2.5 μl, genomic DNA (100 ng/μl) 1 μl and ddH$_2$O 19 μl. PCR amplification procedure was: a pre-denaturing for 5 minutes at 95° C., followed by 32 cycles, containing denaturing at 94° C. for 30 seconds, annealing at 50° C. for 30 seconds, and extension at 72° C. for 1 minute; finally extension at 72° C. for 10 minutes. After gel electrophoresis purification of PCR products, target fragments were recovered with a DNA Recovery Kit. After DNA sequencing, the whole length of the open reading frame encoded in the sequence was 1002 bp and its base sequence is set forth in SEQ ID No. 1.

Example 4 Preparation of Recombinant Expression Plasmid and Recombinant Expression Transformant of Carbonyl Reductase The fragments of carbonyl reductase obtained by PCR amplification in Example 3 and pET 28a blank plasmid were subjected to double digestion with restriction endonucleases EcoR I and Xho I simultaneously overnight, and then gel electrophoresis purification and recovery with a DNA kit. The recovered digested fragments and blank plasmid were linked with the action of T4 DNA ligase at 4° C. for 12 h and the recombinant plasmid pET28a-CpKR was obtained.

The obtained recombinant plasmid was transformed into E. coli DH 5α, which was plated onto LB medium plate containing 50 μg/ml kanamycin, and cultured at 37° C. for 8 h, and the colonies are verified through colony PCR and those with a target band of about 1000 bp after PCR amplification was picked as positive clones. After verification through sequencing, corresponding plasmids were extracted and transformed into E. coli BL21, and the positive clones were picked, which means that the recombinant expression transformant E. coli BL21 (DE3)/pET28a-CpKR was obtained.

Example 5 Inducible Expression of Carbonyl Reductase CpKR

The recombinant expression transformant of E. coli BL21 (DE3)/pET28a-CpKR obtained in Example 4 was inoculated in LB media containing 50 μg/ml kanamycin, cultured with oscillation in a shaker at 37° C. for 12 h, then inoculated in a 500 ml conical flask containing 100 ml LB media at an inoculation rate of 1% (v/v), placed in a shaker at 37° C. and cultured with oscillation at 180 rpm. When the OD$_{600}$ of culture liquid reached 0.7, IPTG was added to the final concentration of 0.2 mmol/L for inducing, and after induction at 16° C. for 24 h, the culture liquid was centrifugated at 8000 rpm, and the cells were collected and washed with normal saline, and the resting cells were obtained. The obtained cells were resuspended in 10 ml Tris-HCl buffer (100 mM, pH 7.0), ultrasonicated in ice bath as follows: working power of 400 W for 4 s, pause for 6 s, for 99 cycles, centrifugated at 4° C. and 10000 rpm for 10 minutes, and the supernatant was collected and determined for activity according to the above methods. The determined enzyme activity was 81.3 U/ml lysate.

Example 6 Preparation of Recombinant Carbonyl Reductase Mutant CpKR$_{G86E}$ The whole length gene sequence of the carbonyl reductase CpKR obtained in Example 3 (SEQ ID No.1) was subjected to base mutation with mutating positions 257 (G→A) and 258 (G→A) respectively in the reductase gene encoding sequence to obtain the base sequence of the mutant gene as set forth in SEQ ID No.3. The encoded amino acid sequence is set forth in SEQ ID No.4, i.e., mutating position 86 (Gly→Glu) of the carbonyl reductase CpKR (SEQ ID No.2), and the carbonyl reductase encoded by the mutant gene is designated as CpKR$_{G86E}$. The recombinant expression plasmid and recombinant expression transformant containing the mutant gene DNA was prepared by the method as described in Example 4, and cultured according to the method of Example 5, after inducible expression, the lysate obtained after ultrasonication was taken and the enzyme activity was determined to be 122 U/ml lysate.

Example 7 Preparation of Recombinant Carbonyl Reductase Double Mutant CpKR$_{G86E/A163S}$ The whole length gene sequence of the carbonyl reductase CpKR obtained in Example 3 (SEQ ID No.1) was subjected to base mutation with mutating positions 257 (G→A), 258 (G→A), 487 (G→T), and 489 (T→G) in the reductase gene encoding sequence to obtain the base sequence of the mutant gene as set forth in SEQ ID No.5. The encoded amino acid sequence is set forth in SEQ ID No.6, i.e., mutating position 86 (Gly→Glu) and 163 (Ala→Ser) of the carbonyl reductase CpKR (SEQ ID No.2), and the carbonyl reductase encoded by the mutant gene is designated as CpKR$_{G86E/A163S}$. The recombinant expression plasmid and recombinant expression transformant containing the mutant gene DNA sequence were prepared by the method as described in Example 4, and cultured according to the method of Example 5, after inducible expression, the lysate obtained after ultrasonication was taken and the enzyme activity was determined to be 181 U/ml lysate.

Example 8 CpKR Catalyzes Asymmetric Reduction of ethyl 6-carbonyl-8-chlorocaprylate 0.1 ml culture liquid in Example 5 was taken and centrifugated at 10000 rpm for 5 minutes, and precipitated cells were resuspended in 1 ml potassium phosphate buffer (100 mM, pH 7.0), and 0.01 mmol ethyl 6-carbonyl-8-chlorocaprylate (i.e., concentration is 10 mM) was added and NADPH was added to the final concentration of 10 mmol/L, then placed on a constant temperature mixing apparatus for reaction at 30° C. and 1000 rpm for 12 h. Sampling, and extracting with equal volume of ethyl acetate, the extract was dried with anhydrous sodium sulfate for 8 h, analyzed through gas chromatography with a conversion rate of 98.7%. The product was acetylized prior to gas chromatography and the optical purity thereof was determined to be 97% ee (R).

Example 9 CpKR Catalyzes Asymmetric Reduction of ethyl 6-carbonyl-8-chlorocaprylate Reaction was conducted in a 2 mL centrifuge tube. 20 mmol/L substrate ethyl 6-carbonyl-8-chlorocaprylate, 6 g/L glucose, 1 U glucose dehydrogenase and $NADP^+$ with a final concentration of 1.0 mM were added into 1 mL Tris-HCl buffer (100 mmol/L, pH 7.0), and the resting cells that recombinantly expressing CpKR as described in Example 5 were added with an amount of 53 U enzyme/mmol substrate. Reaction was conducted on a mixing apparatus at 1000 rpm and 30° C. After conversion for 10 h, the conversion rate of substrate was determined to be 99.2%, and the ee value of the product was 99.7% (R).

Example 10 Asymmetric Reduction of Ethyl 6-Carbonyl-8-Chlorocaprylate by Recombinant Reductase $CpKR_{G86E}$ Reaction was conducted in a 2 mL centrifuge tube. 20 mmol/L substrate ethyl 6-carbonyl-8-chlorocaprylate, 6 g/L glucose and 1 U glucose dehydrogenase were added into 1 mL Tris-HCl buffer (100 mmol/L, pH 7.0), and the resting cells that recombinantly expressing $CpKR_{G86E}$ as described in Example 6 were added with an amount of 10 U enzyme/mmol substrate. Reaction was conducted on a mixing apparatus at 1000 rpm and 30° C. After conversion for 8 h, the conversion rate of substrate was determined to be 99.1%, and the ee value of the product was 97.3% (R).

Example 11 Asymmetric Reduction of Ethyl 6-Carbonyl-8-Chlorocaprylate by Recombinant Reductase $CpKR_{G86E/A163S}$ Reaction was conducted in a 2 mL centrifuge tube. 20 mmol/L substrate ethyl 6-carbonyl-8-chlorocaprylate, 6 g/L glucose and 1 U glucose dehydrogenase were added into 1 mL Tris-HCl buffer (100 mmol/L, pH 7.0), and the resting cells that recombinantly expressing $CpKR_{G86E/A163S}$ as described in Example 7 were added with the amount of 8 U enzyme/mmol substrate. Reaction was conducted on a mixing apparatus at 1000 rpm and 30° C. After conversion for 10 h, the conversion rate of substrate was determined to be 99.5%, and the ee value of the product was 99.6% (R).

Example 12 Gene Tandem Co-Expression of Carbonyl Reductase and Glucose Dehydrogenase According to conventional PCR amplification and enzyme digestion and ligation, the carbonyl reductase $CpKR_{G86E/A163S}$ gene as set forth in SEQ ID No. 6 was amplified with primers CpKR-Nde I and CpKR-EcoR I; the target gene and plasmid pET 28a were subjected to double digestion with Nde I/EcoR I, then linked and transformed into E. coli BL21 (DE3), and plasmid pET28-$CpKR_{G86E/A163S}$ was extracted; the target gene of glucose dehydrogenase BmGDH as set forth in SEQ ID No. 14 was amplified with primers BmGDH-Sal I and BmGDH-Xho I; after Sal I/Xho I double digestion of BmGDH and plasmid pET28-$CpKR_{G86E/A163S}$ containing CpKR fragments, they were linked and transformed into E. coli BL21 (DE3), i.e., the recombinant expression transformant E. coli BL21 (DE3) containing $CpKR_{G86E/A163S}$ and BmGDH (pET28-$CpKR_{G86E/A163S}$-BmGDH) was obtained.

E. coli BL21 (DE3) (pET28-$CpKR_{G86E/A163S}$-BmGDH) was inoculated in LB culture media containing 50 μg/ml kanamycin, and cultured in a shaker at 37° C. for 12 h, then inoculated in a 500 ml conical flask containing 100 ml LB media at the inoculation rate of 1% (v/v), placed in a shaker at 37° C. and cultured with oscillation at 180 rpm. When the $OD_{600}$ of culture liquid reached 0.7, IPTG was added to the final concentration of 0.2 mmol/L for inducing, after induction at 16° C. for 24 h, the culture liquid was centrifugated at 8000 rpm, the cells were collected and washed with normal saline, and the resting cells were obtained. After lyophilization, the lyophilizated recombinant expression transformant (E. coli BL21/pET28a-$CpKR_{G86E/A163S}$-BmGDH) was obtained and the $CpKR_{G86E/A163S}$ activity thereof was determined to be 8.0 U/mg lyophilizated cells, and BmGDH activity was 3.4 U/mg lyophilizated cells.

Examples 13~19 Carbonyl Asymmetric Reduction by Co-Expression Whole Cells 0.1 g of the lyophilizated cells of the recombinant expression transformant (E. coli BL21/pET28a-$CpKR_{G86E/A163S}$-BmGDH) in Example 12 were added into 10 mL Tris-HCl buffer (100 mmol/L, pH 7.0), and corresponding carbonyl compound substrate was added to reach the final concentration of 100 mmol/L, and glucose was added to reach 150 mmol/L and $NADP^+$ was added to reach 0.1 mmol/L. Reaction solution was subjected to magnetic stirring at 30° C., and 1 mol/L sodium carbonate solution was fed to maintain pH at 7.0. After reaction for 1 h, the reaction was stopped and extracted with equal volume of ethyl acetate twice, and the extract was combined and dried with anhydrous sodium sulfate overnight, and the conversion rate of substrate and the ee value of the product were determined. Analysis conditions for the conversion rate and ee value can refer to Adv Synth Catal 2012, 354, 1765-1772; Appl Microbiol Biotechnol. 2007, 76, 237-248. The results are shown in Table 1:

TABLE 1

Results of carbonyl reduction reaction catalyzed by CpKR

| Example | Substrate | Product | Conversion | ee value (%) |
|---|---|---|---|---|
| 13 | (structure) | (structure) | >99% | 99 (R) |

TABLE 1-continued

Results of carbonyl reduction reaction catalyzed by CpKR

| Example | Substrate | Product | Conversion | ee value (%) |
|---|---|---|---|---|
| 14 | ethyl 4-chloro-3-oxobutanoate | ethyl (R)-4-chloro-3-hydroxybutanoate | >99% | 93 (R) |
| 15 | ethyl 3-oxopentanoate | ethyl (R)-3-hydroxypentanoate | >99% | 100 (R) |
| 16 | ethyl 3-oxohexanoate | ethyl (R)-3-hydroxyhexanoate | >99% | 100 (R) |
| 17 | ethyl 8-chloro-6-oxooctanoate | ethyl (R)-8-chloro-6-hydroxyoctanoate | >99% | 97 (R) |
| 18 | methyl 2-(2-chlorophenyl)-2-oxoacetate | methyl (R)-2-(2-chlorophenyl)-2-hydroxyacetate | >99% | 93 (R) |
| 19 | ethyl 2-oxo-4-phenylbutanoate | ethyl (R)-2-hydroxy-4-phenylbutanoate | >99% | 93 (R) |

Example 20 Catalytic Reduction of 100 mmol/L ethyl 6-carbonyl-8-chlorocaprylate with Lyophilizated Cells To 10 mL Tris-HCl buffer (100 mmol/L, pH 7.0) containing 100 mmol/L substrate ethyl 6-carbonyl-8-chlorocaprylate (22 g/L) and 150 mmol/L glucose, 0.1 g of the lyophilizated cells of the recombinant expression transformant (*E. coli* BL21/pET28a-CpKR$_{G86E/A163S}$-BmGDH) as described in Example 12 were added. Reaction was subjected to magnetic stirring at 30° C., 1 mol/L sodium carbonate solution was fed through an automatic potentiometric titrator to maintain pH at 7.0. After reaction for 3 h, the reaction was extracted with equal volume of ethyl acetate twice, and the extract was combined and dried with anhydrous sodium sulfate overnight. The conversion rate of substrate was 99.4% and the ee value of the product was 99.8%, as determined by gas chromatography.

Example 21 Catalytic Reduction of 1.5 mol/L ethyl 6-carbonyl-8-chlorocaprylate with Lyophilizated Cells To 10 mL Tris-HCl buffer (100 mmol/L, pH 7.0) containing 1.5 mol/L substrate ethyl 6-carbonyl-8-chlorocaprylate and 2.25 mol/L glucose, 0.3 g of the lyophilizated cells of the recombinant expression transformant (*E. coli* BL21/pET28a-CpKR$_{G86E/A163S}$-BmGDH) as described in Example 12 were added. Reaction was subjected to magnetic stirring at 30° C., 1 mol/L sodium carbonate solution was fed through an automatic potentiometric titrator to maintain pH at 7.0. After reaction for 12 h, the reaction was extracted with equal volume of ethyl acetate twice, and the extract was combined and dried with anhydrous sodium sulfate overnight. The conversion rate of substrate was 99.9% and the ee value of the product was 99.8%, as determined by gas chromatography. Solvent was removed through rotary evaporation and 2.93 g product was obtained with an isolation yield of 88%.

Example 22 Reduction of Ethyl 6-Carbonyl-8-Chlorocaprylate with 1-L Scale of Whole Cells To 1 L Tris-HCl buffer (100 mmol/L, pH 7.0) containing 1 mol/L substrate ethyl 6-carbonyl-8-chlorocaprylate and 1.5 mol/L glucose, 10 g of the lyophilizated cells of the recombinant expression transformant (*E. coli* BL21/pET28a-CpKR$_{G86E/A163S}$-BmGDH) as described in Example 6 were added. Reaction was subjected to mechanical stirring at 30° C. in a water bath, and 1 mol/L sodium carbonate solution was fed through an automatic potentiometric titrator to maintain the pH at 7.0. After reaction for 8 h, the conversion rate was determined to be 99.9% and the ee value of the product was 99.8%. The reaction was extracted with equal volume of ethyl acetate twice, and the extract was combined and dried with anhydrous sodium sulfate overnight. Solvent was removed through rotary evaporation and 198 g product was obtained with an isolation yield of 90%. The specific rotation of the product was determined as $[\alpha]_{25}^{D}=-21.0°$ (c 1.0, ethanol).

Comparative Example 1

The effect of asymmetric reduction of ethyl 6-carbonyl-8-chlorocaprylate by the carbonyl reductase CpKR of the disclosure was compared with the catalytic effects reported in references. Comparison of reaction system and catalytic results was summarized in Table 2.

TABLE 2

Comparison of the catalytic reaction effects of ethyl 6-carbonyl-8-chlorocaprylate by CpKR with the the reported levels in references

| Biligical Catalyst | Substrate Concentration (g/L) | Additional Coenzyme (mM) | Time (h) | Conversion (%) | ee (%) | Data Resource |
|---|---|---|---|---|---|---|
| Geotrichum candidum | 5 | 0 | 24 | 62 | 88 (R) | U.S. Pat. No. 7,135,328 B2 |
| TbADH | 2 | 0.5 | — | >85 | >99.5 (R) | U.S. Pat. No. 7,157,253 B2 |
| NgADH | 44 | 4 | 24 | 95 | — | WO 2007028729A1 |
| MzCR | 85 | 0.1 | 24 | 55 | >97 (R) | WO 2005049816 A2 |
| Rhodococcus baikonurensis | 66 | 0 | 36 | >99 | 93 (R) | CN103451124 A |
| CpKR | 330 | 0 | 12 | >99 | 99.8 (R) | Present invention, Example 21 |

Particularly, Olbrich et al. used the whole cells of *Geotrichum candidum* to catalyze asymmetric reduction of methyl 6-carbonyl-8-chlorocaprylate to methyl (R)-6-hydroxy-8-chlorocaprylate, and the cultured *Geotrichum candidum* cells were suspended in buffer containing 5 g/L glucose with equal volume of fermentation liquid for reaction, wherein the concentration of substrate was only 5 g/L. After reaction for 24 h, the yield was only 62% and the ee value of the product was only 88% (see in U.S. Pat. No. 7,135,328 B2).

Müller et al. used alcohol dehydrogenase TbADH from *Thermoanaerobium brokii* to catalyze asymmetric reduction of 6-carbonyl-8-chlorocaprylate to generate (R)-6-hydroxy-8-chlorocaprylate, coenzyme regeneration was performed by formate dehydrogenase. The concentration of alcohol dehydrogenase TbADH and formate dehydrogenase were both 4 kU/L, and the substrate concentration was only 2 g/L. The reaction was conducted at 37° C., the optical purity of the generated (R)-6-hydroxy-8-chlorocaprylate can be 99.5%, but its conversion was only 85%, and 0.5 mM coenzyme and 1 mM dithiothreitol (DTT) were also required in the reaction system (see in U.S. Pat. No. 7,157,253 B2).

Werner et al. used NgADH from *Nocardia globulera* to prepare (R)-6-hydroxy-8-chlorocaprylate. The substrate concentration can be 44 g/L and the concentration of dehydrogenase was 58 U/mmol substrate. The reaction was conducted at 30° C. for 24 h, the conversion was 95%, but the ee value of the product thereof is not shown (see in WO 2007/028729 A1, 2007).

Gupta et al. used an oxidoreductase from *Metschnikowia zobellii* to catalyze reaction in a two-phase system, and 25 U/ml recombinant oxidoreductase MzCR, 5 U/ml alcohol-dehydrogenase and 0.1 mM NADP+ were added to the reaction system. The reaction was conducted at 25° C., which catalyzes the conversion of 85 g/L substrate 6-carbonyl-8-chlorocaprylate into the product (R)-6-hydroxy-8-chlorocaprylate, and the ee value of the product was 97%, and after reaction for 24 h, the conversion was only 55% (see in WO 2005049816 A2).

Chen et al. used 300 g/L *Rhodococcus baikonurensis* resting cells and crude enzyme solution of 60 kU/L glucose dehydrogenase, at 30° C. and pH 6.0, and the reaction for 36 h only catalyzed conversion of 300 mM ethyl 6-carbonyl-8-chlorocaprylate, and the ee value of the product was only 93% (see in CN103451124A).

As illustrated in various examples of the disclosure, particularly in Table 2, the technology of the disclosure can be used to catalyze a substrate with a concentration (e.g., 330 g/L) that is much higher than the highest one reported (85 g/L) in the prior art, and the conversion rate and the optical purity of the product are also very high.

After reading the above description, a person skilled in the art will appreciate that changes and modifications may be made thereto, and it is intended to include all such changes and modifications as fall within the true scope of the invention.

What claimed is:

1. A *Candida parapsilosis* with the deposit number CGMCC 9630, wherein the *Candida parapsilosis* recombinantly expresses a carbonyl reductase, wherein the amino acid sequence of the carbonyl reductase is as set forth in SEQ ID Nos. 2, 4 or 6.

2. A recombinant and isolated carbonyl reductase encoding gene, wherein the gene is:
   (1) a nucleotide sequence as set forth in SEQ ID Nos. 1, 3 or 5;
   (2) an encoding gene of a protein with an amino acid sequence as set forth in SEQ ID Nos. 2, 4 or 6.

3. A recombinant expression vector, wherein the vector comprises the gene according to claim 2, and optionally an encoding gene of a glucose dehydrogenase, wherein the glucose dehydrogenase is as set forth in SEQ ID No. 14.

4. A recombinant expression transformant, wherein the transformant comprises the recombinant expression vector according to claim 3.

5. A method of preparing a carbonyl reductase, wherein the method comprises a step of culturing the *Candida parapsilosis* according to claim 1.

6. The method of claim 5, further comprising catalyzing an asymmetric reduction reaction of prochiral carbonyl compounds using the carbonyl reductase as a catalyst in the reduction reaction in vitro.

7. The method according to claim 6, wherein the concentration of the prochiral carbonyl compounds is 1 to 1500 mmol/L, and the amount of the carbonyl reductase is 8.0-800 U per mmol of prochiral carbonyl compounds.

8. The method according to claim 6, wherein in the asymmetric reduction reaction, the following is further added:
   (1) 0 to 10 mmol/L of coenzyme NADPH; or
   (2) 0 to 340 U of glucose dehydrogenase per mmol of prochiral carbonyl compounds, 0 to 0.3 g of glucose per mmol of prochiral carbonyl compounds, and 0 to 1.0 mmol/L of NADP$^+$.

9. The method according to claim 6, wherein the prochiral carbonyl compounds are selected from the followings:

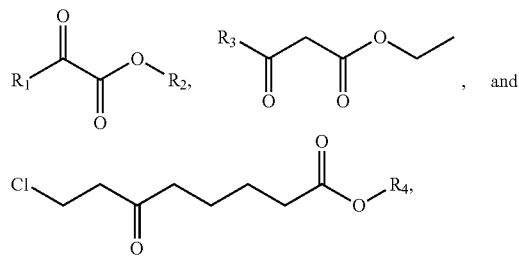

, and wherein $R_1$ is selected from —$CH_2(CH_3)_2$, -2-Cl—$C_6H_4$ and —$(CH_2)_2C_6H_5$; $R_2$ is —$CH_3$ or —$CH_2CH_3$; $R_3$ is —$CH_2C_1$, —$CH_2CH_3$ or —$(CH_2)_2CH_3$; $R_4$ is —$CH_3$ or —$CH_2CH_3$.

10. The method according to claim 9, wherein the prochiral carbonyl compound is ethyl 6-carbonyl-8-chlorocaprylate.

* * * * *